US011857861B2

(12) United States Patent
Sachs et al.

(10) Patent No.: US 11,857,861 B2
(45) Date of Patent: Jan. 2, 2024

(54) ATHLETIC RECOVERY SYSTEM COMBINING COGNITIVE AND PHYSICAL ASSESSMENTS

(71) Applicant: Rewire Fitness, Inc., New Paltz, NY (US)

(72) Inventors: Sun Sachs, New Paltz, NY (US); Cody Frances Rotwein, Wappingers Falls, NY (US); Edward James Gibbins, London (GB)

(73) Assignee: Rewire Fitness, Inc., New Paltz, NY (US)

( * ) Notice: Subject to any disclaimer, the term of this patent is extended or adjusted under 35 U.S.C. 154(b) by 7 days.

(21) Appl. No.: 17/886,412

(22) Filed: Aug. 11, 2022

(65) Prior Publication Data

US 2022/0401814 A1 Dec. 22, 2022

Related U.S. Application Data

(63) Continuation of application No. 16/799,458, filed on Feb. 24, 2020, now Pat. No. 11,452,927.
(Continued)

(51) Int. Cl.
*G09B 19/00* (2006.01)
*A63B 71/06* (2006.01)
*A63B 24/00* (2006.01)

(52) U.S. Cl.
CPC ...... *A63B 71/0622* (2013.01); *A63B 24/0062* (2013.01); *A63B 2071/0663* (2013.01); *A63B 2225/50* (2013.01)

(58) Field of Classification Search
CPC ............ A63B 24/0062; A63B 71/0619; A63B 71/0622; A63B 2225/50
See application file for complete search history.

(56) References Cited

U.S. PATENT DOCUMENTS 4,166,452 A 9/1979 Generales, Jr.
4,199,987 A 4/1980 Bauers et al.
(Continued)

OTHER PUBLICATIONS

International Search Report and Written Opinion for International Application No. PCT/US2020/019518, dated May 11, 2020.
(Continued)

*Primary Examiner* — Alvin A Hunter
(74) *Attorney, Agent, or Firm* — Wolf, Greenfield & Sacks, P.C.

(57) ABSTRACT

A method for cognitive brain training, psychological motivation, and recovery to be used in conjunction with physical exercise in order to reduce the effects of mental and physical fatigue and improve athletic performance. A plurality of input devices integrate ergonomically with different sports so as not to limit movement, eye-hand coordination or negatively impact physical training. Software, executable on a portable computing device is configured for a sport, enabling an athlete to perform physical and cognitive tasks at the same time. Metrics, formulas and algorithms combine the athlete's self-rated performance with real-time cognitive and physiological output metrics to provide reports of the athlete's performance for each workout and for all workouts overtime. Mental recovery and motivation protocols used to help athletes stay on task and recover from the physical training. Cognitive fatigue self-assessment tests used to help athletes determine their current level of mental fatigue and readiness to train.

22 Claims, 22 Drawing Sheets

Flow chart summarizing selected operational details of the brain training software

Related U.S. Application Data

(60) Provisional application No. 62/809,927, filed on Feb. 25, 2019.

(56) References Cited

U.S. PATENT DOCUMENTS

| | | | |
|---|---|---|---|
| 4,464,121 A | 8/1984 | Perelli | |
| 4,534,557 A | 8/1985 | Bigelow et al. | |
| 4,645,458 A | 2/1987 | Williams | |
| 4,702,475 A | 10/1987 | Elstein et al. | |
| 4,751,642 A | 6/1988 | Silva et al. | |
| 5,230,629 A | 7/1993 | Buschke | |
| 5,595,488 A | 1/1997 | Gozlan et al. | |
| 5,901,961 A | 5/1999 | Holland, III | |
| 5,911,581 A | 6/1999 | Reynolds et al. | |
| 6,066,105 A | 5/2000 | Guillen | |
| 6,113,538 A | 9/2000 | Bowles et al. | |
| 6,241,686 B1 | 6/2001 | Balkin et al. | |
| 6,416,472 B1 | 7/2002 | Cady et al. | |
| 6,712,615 B2 | 3/2004 | Martin | |
| 6,722,888 B1* | 4/2004 | Macri | A63F 13/428 463/3 |
| 6,749,432 B2* | 6/2004 | French | G09B 19/0038 434/362 |
| 8,627,355 B2* | 1/2014 | Lanfermann | A63B 24/0006 725/42 |
| 9,028,258 B2* | 5/2015 | Burdea | A61B 5/375 482/50 |
| 9,248,358 B2* | 2/2016 | Tinjust | A63B 71/0622 |
| 9,415,263 B2* | 8/2016 | DeCarlo | A63B 63/00 |
| 9,564,058 B2* | 2/2017 | Reichow | A63B 24/0087 |
| 9,573,035 B2* | 2/2017 | DeCarlo | A63B 63/00 |
| 9,782,648 B2* | 10/2017 | DeCarlo | A61B 5/6895 |
| 9,901,780 B2* | 2/2018 | DeLuca | A61B 5/68 |
| 10,155,148 B2* | 12/2018 | Reichow | A63B 22/0605 |
| 10,380,910 B2 | 8/2019 | Wu et al. | |
| 10,478,698 B2* | 11/2019 | Tinjust | G09B 19/0038 |
| 10,532,000 B1* | 1/2020 | De Sapio | A63B 24/0062 |
| 10,610,143 B2* | 4/2020 | Tinjust | G09B 19/0038 |
| 10,635,267 B2* | 4/2020 | Williams | A61B 5/0205 |
| 10,653,938 B1* | 5/2020 | Traustason | A63B 63/00 |
| 10,795,466 B1* | 10/2020 | Lo | G06F 3/0362 |
| 10,888,762 B2* | 1/2021 | Cohen | G09B 19/0038 |
| 11,141,092 B2* | 10/2021 | Stephens | A63G 31/00 |
| 11,452,927 B2* | 9/2022 | Sachs | G16H 20/30 |
| 2009/0281450 A1 | 11/2009 | Reichow et al. | |
| 2016/0267809 A1 | 9/2016 | deCharms et al. | |
| 2017/0361164 A1 | 12/2017 | Rueckmann | |
| 2020/0269123 A1 | 8/2020 | Sachs et al. | |

OTHER PUBLICATIONS

International Preliminary Report on Patentability for International Application No. PCT/US2020/019518, dated Sep. 2, 2021.

[No Author Listed], Axon Sports—Performance & Cognitive Training. Axon Sports. 2 pages. URL:https://www.axonsports.com [retrieved on May 20, 2020].

[No Author Listed], Brain Training, Brain Games, Memory Games, and Brain Fitness with CogniFit. CogniFit. 3 pages. URL:https://www.cognifit.com [retrieved on May 19, 2020].

[No Author Listed], Calm—The #1 App for Meditation and Sleep. Calm. 2 pages. URL:https://www.calm.com [retrieved on May 18, 2020].

[No Author Listed], Halo Neurosciene—Upgrade Your Brain. Halo. 3 pages. URL:https://www.haloneuro.com [retrieved on May 18, 2020].

[No Author Listed], Home—Optios. Optios. 15 pages. URL:https://www.platypusneuro.com (redirects to: https://optios.com) [retrieved on May 18, 2020].

[No Author Listed], Home—Sanvello. Sanvello. 9 pages. URL:https://www.sanvello.com [retrieved on May 18, 2020].

[No Author Listed], Lumosity Brain Training: Challenge & Improve Your Mind. Lumosity. 3 pages. URL:https://www.lumosity.com [retrieved on May 19, 2020].

[No Author Listed], Meditation and Sleep Made Simple—Headspace. 3 pages. URL:https://www.headspace.com [retrieved on May 18, 2020].

[No Author Listed], Muse—Meditation Made Easy with the Muse Headband. Muse. 3 pages. URL:https://choosemuse.com [retrieved on May 20, 2020].

[No Author Listed], Peak Brain Training—Level Up Your Brain! Peak. 10 pages. URL:https://www.peak.net [retrieved on May 18, 2020].

[No Author Listed], Performance—Athletics. NeuroTracker. 2 pages. URL:https://neurotracker.net/performance [retrieved on May 19, 2020].

[No Author Listed], Re:Brain—by Actum. Actum Technology Corp. 12 pages. URL:http://actumtechnology.com [retrieved on May 18, 2020].

[No Author Listed], sswitch—Limits Can be Manipulated. Sswitch. 8 pages. URL:https://sswitch.ch [retrieved on May 18, 2020].

[No Author Listed], TB12 & BrainHQ. Posit Science. 5 pages. URL:https://tb12.brainhq.com [retrieved on May 18, 2020].

[No Author Listed], The Sufferfest Mental Training Programme. Sufferfest. 5 pages. URL:https://thesufferfest.com/pages/learn-more-mind (redirects to: https://thesufferfest.com/pages/mental-toughness) [retrieved on May 19, 2020].

Axelsen et al., On-the-Spot Binaural Beats and Mindfulness Reduces the Effect of Mental Fatigue. Journal of Cognitive Enhancement. 2020:4:31-39. doi:10.1007/s41465-019-00162-3.

Bernstein, 'Self Talk': When Talking to Yourself, the Way You Do It Makes a Difference. May 5, 2014. 4 pages. URL:https://www.wsj.com/articles/self-talk-when-talking-to-yourself-the-way-you-do-it-makes-a-difference-1399330343 [retrieved on May 4, 2020].

Blanchfield et al., Non-conscious visual cues related to affect and action alter perception of effort and endurance performance. Frontiers in Human Neuroscience. 2014;8(967):1-16. doi: 10.3389/fnhum.2014.00967.

Blanchfield et al., Talking Yourself Out of Exhaustion: The Effects of Self-talk on Endurance Performance. Medicine & Science in Sports & Exercise. 2013;46(5):998-1007. 11 pages. doi:10.1249/MSS.0000000000000184.

Brooks, The Wisdom Your Body Knows. Nov. 28, 2019. 2 pages. URL:https://www.nytimes.com/2019/11/28/opinion/brain-body-thinking.html [retrieved on May 4, 2020].

Brownsberger et al., Impact of Mental Fatigue on Self-paced Exercise. Int J Sports Med. 2013. 10 pages. doi: 10.1055/s-0033-1343402.

Cutsem et al., The Effects of Mental Fatigue on Physical Performance: A Systematic Review. Sports Medicine. 2017. pp. 1569-1588. 84 pages. doi: 10.1007/s40279-016-0672-0. Retrieved from Internet: URL:https://kar.kent.ac.uk/60767/1/SPOA-D-16-00188_R4.pdf.

Davis, Tom Brady uses brain exercises designed for people with brain impairments and it blew away the scientists who created them. Jan. 29, 2019. 5 pages. URL:https://www.businessinsider.com/tom-brady-brain-exercises-improve-function-2017-10 [retrieved on May 4, 2020].

Heisz et al., The Effects of Physical Exercise and Cognitive Training on Memory and Neurotrophic Factors. Journal of Cognitive Neuroscience. 2017;29(11): 1895-1907. doi:10.1162/jocn_a_01164.

Hutchinson, The Mental Tricks of Athletic Endurance. Feb. 2, 2018. 7 pages. URL:https://www.wsj.com/articles/the-mental-tricks-of-athletic-endurance-1517583851 [retrieved on May 4, 2020].

Jones, What Is This Thing Called Mental Toughness? An Investigation of Elite Sport Performers. Journal Of Applied Sport Psychology. 2002; 14:205-218. 14 pages. doi:10.1080/10413200290103509.

Keating, The secrets of endurance athletes. Nov. 6, 2018. 14 pages. URL:https://www.bbc.com/future/article/20181106-the-secrets-of-endurance-athletes [retrieved on May 4, 2020].

Lefave, How Mental Fatigue Can Actually Sabotage Your Endurance. May 31, 2018. 7 pages. URL:https://www.runnersworld.com/training/a20797674/how-fatigue-affects-endurance [retrieved on May 4, 2020].

(56) References Cited

OTHER PUBLICATIONS

Marcora et al., Mental fatigue impairs physical performance in humans. Journal of Applied Physiology. 2009;106(3):857-864. doi:10.1152/japplphysiol.91324.2008.

Martin et al., Mental Fatigue Impairs Endurance Performance: A Physiological Explanation. Sports Medicine. 2018. 14 pages. doi: 10.1007/s40279-018-0946-9.

Martin et al., Superior Inhibitory Control and Resistance to Mental Fatigue in Professional Road Cyclists. PLOS One. 2016;11(7):e0159907. 15 pages. doi: 10.1371/journal.pone.0159907.

Pageaux et al., Response inhibition impairs subsequent self-paced endurance performance. European Journal of Applied Physiology. 2014; 114:1095-1105. 11 pages. doi:10.1007/s00421-014-2838-5.

Reynolds, Exercise May Enhance the Effects of Brain Training. The New York Times. Nov. 22, 2017. 2 pages. URL:https://www.nytimes.com/2017/11/22/well/move/exercise- may-enhance-the-effects-of-brain-training.html [retrieved on May 4, 2020].

Russell et al., The application of mental fatigue research to elite team sport performance: New perspectives. Journal of Science and Medicine in Sport. 2019;22(6):723-728. doi:10.1016/j.jsams.2018.12.008.

Schmeichel et al., Self-Affirmation and Self-Control: Affirming Core Values Counteracts Ego Depletion. Journal of Personality and Social Psychology. 2009;96(4): 770-782. doi: 10.1037/a0014635.

Schonbrun, Keep Your Eye on the Balls to Become a Better Athlete. Jan. 4, 2017. 5 pages. URL:https://www.nytimes.com/2017/01/04/sports/neurotracker-athletic-performance.html [retrieved on May 4, 2020].

Sneed, The performance enhancer for your brain: How elite athletes are using EEG to get a mental edge. Sports Illustrated. Feb. 27, 2017. 7 pages. URL:https://www.si.com/edge/2017/02/27/head-in-the-game-book-excerpt-eeg-training-athletes [retrieved on May 4, 2020].

Staiano et al., A Randomized Controlled Trial of Brain Endurance Training (BET) to Reduce Fatigue During Endurance Exercise. American College of Sports Medicine (ACSM) Annual Meeting, San Diego, CA. May 2015. 2 pages.

Staiano et al., Chapter 11 The cardinal exercise stopper: Muscle fatigue, muscle pain or perception of effort ?. Progress in Brain Research. 2018:240:175-200. doi: 10.1016/bs.pbr.2018.09.012.

Staiano et al., Impact Of 4-Week Brain Endurance Training (BET) On Cognitive and Physical Performance In Professional Football Players. Medicine & Science in Sports & Exercise. Jun. 2019. 2 pages. doi: 10.1249/01.mss.0000563395.36093.aa.

\* cited by examiner

FIG. 1A
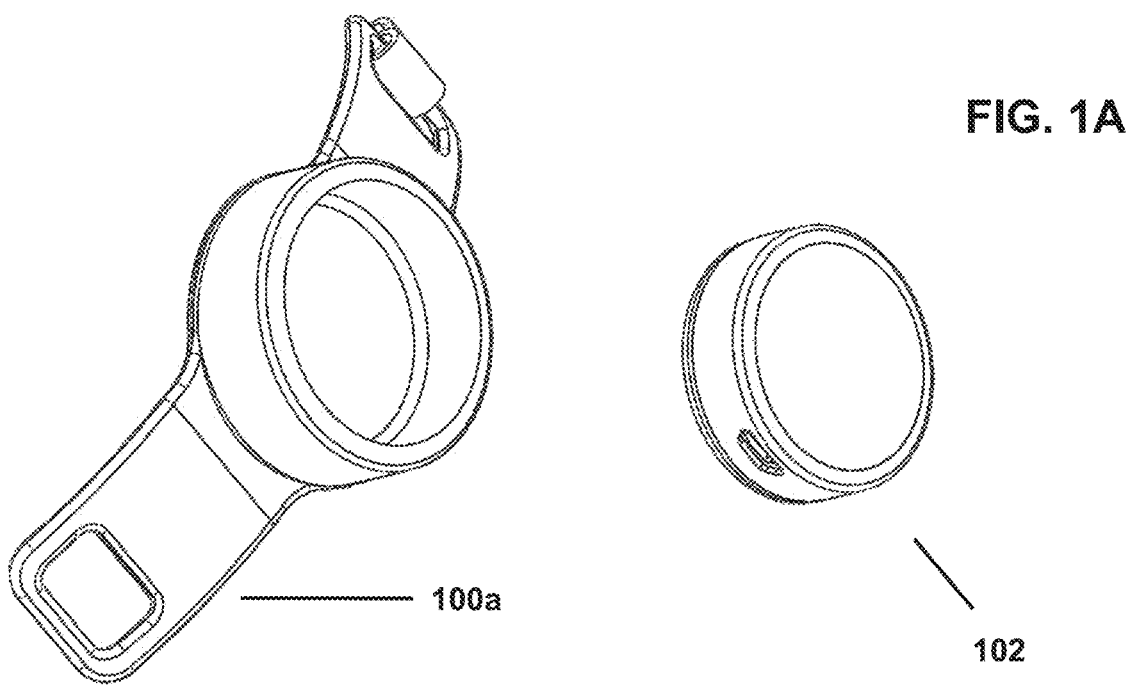
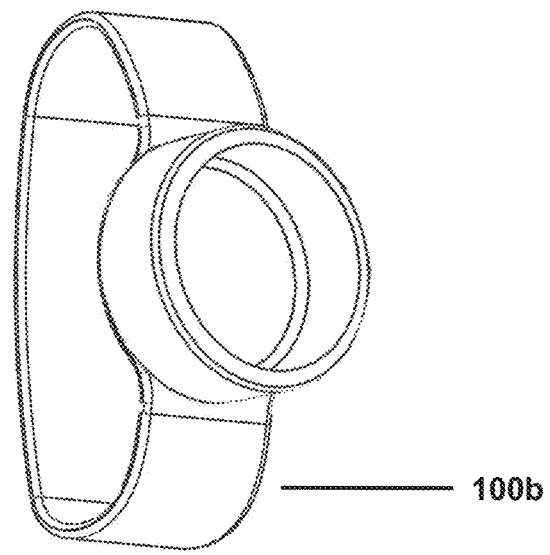
Tactile-Based input apparatus with button and strap Tactile-Based input apparatus with button and strap in exploded view Tactile-Based input apparatus with buttons and straps for bicycle use case Tactile-Based input apparatus with buttons and straps for the hand use case Gesture-based input device with sensors to detect hand movement Voice-based input system for sending and receiving voice commands

134

Selection screen for various cognitive and physical workout programs

136

138

Self-rating calibration system used at the start of the workout

Example of cognitive training and testing interface screen

Coded messages sent wirelessly from input device to smartphone

FIG. 9
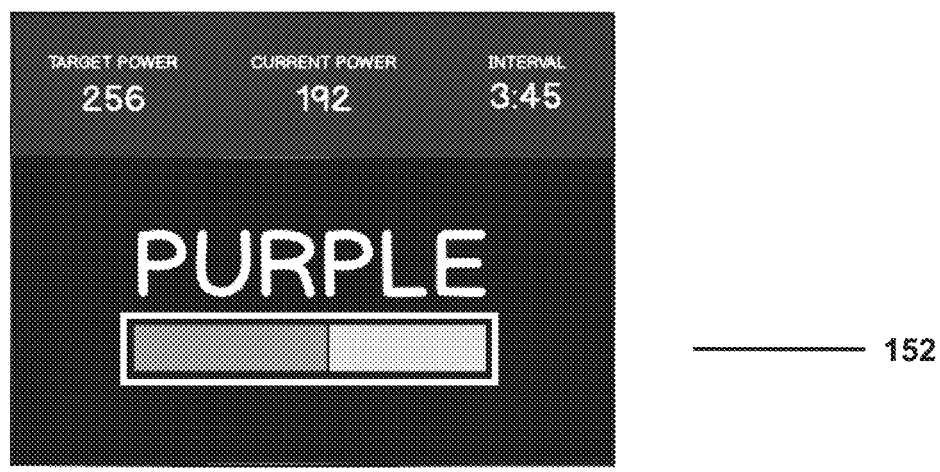
— 152
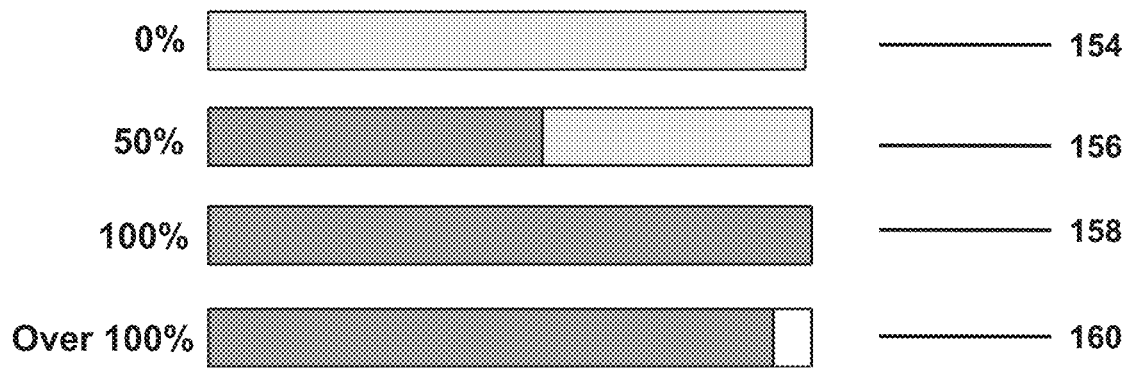
— 154
— 156
— 158
— 160
Physiological target goals represented visually as a progress bar Aggregate quantitative and qualitative self-rating system at end of each workout End of workout report with cognitive and physical metrics Cumulative report of all workouts over time

FIG. 13

182 — Expected RPE Lookup Table Based on Functional Threshold Power (FTP)

| | A | B | C | D |
|---|---|---|---|---|
| | Expected RPE | FTP % (Avg) | Athlete's Average Power Lookup | Training Level |
| | 6 | 30% | 82 | Active Recovery |
| | 7 | 40% | 109 | Active Recovery |
| | 8 | 50% | 136 | Active Recovery |
| 184 | 9 | 55% | 150 | Active Recovery |
| | 10 | 60% | 163 | Endurance |
| | 11 | 68% | 185 | Endurance |
| | 12 | 75% | 204 | Endurance |
| | 13 | 83% | 226 | Tempo |
| | 14 | 90% | 245 | Tempo |
| | 15 | 98% | 267 | Lactate Threshold |
| | 16 | 105% | 286 | Lactate Threshold |
| | 17 | 113% | 307 | Vo2 Max |
| | 18 | 120% | 326 | Vo2 Max |
| | 19 | 150% | 408 | Anaerobic |
| | 20 | 151% | 411 | Neuromuscular |

186 — Expected RPE Lookup Table Based on Lactate Threshold Heart Rate (LTHR)

| A | B | C | D |
|---|---|---|---|
| Expected RPE | LTHR% (Avg) | Athlete's Average Heart Rate Lookup | Training Level |
| 6 | 50% | 85 | Active Recovery |
| 7 | 53% | 90 | Active Recovery |
| 8 | 62% | 105 | Active Recovery |
| 9 | 68% | 116 | Active Recovery |
| 10 | 74% | 126 | Endurance |
| 11 | 79% | 134 | Endurance |
| 12 | 83% | 141 | Endurance |
| 13 | 89% | 151 | Tempo |
| 14 | 94% | 160 | Tempo |
| 15 | 100% | 170 | Lactate Threshold |
| 16 | 104% | 177 | Lactate Threshold |
| 17 | 105% | 179 | Vo2 Max |
| 18 | 106% | 180 | Vo2 Max |
| 19 | N/A | N/A | Anaerobic |
| 20 | N/A | N/A | Neuromuscular |

Lookup tables designed to compare an athlete's self-rated performance with physiological and cognitive output metrics

Positive self-talk mantras that are displayed during training sessions at specific intervals Positive self-talk configuration and personalization screen FIG. 16A
FIG. 16B
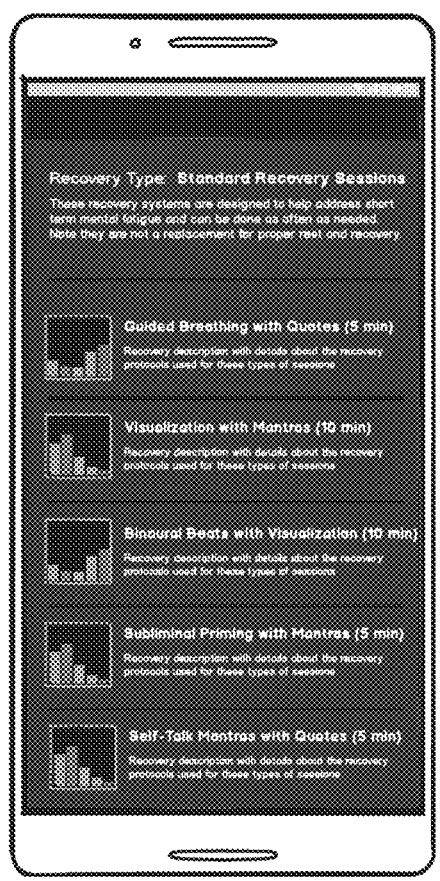
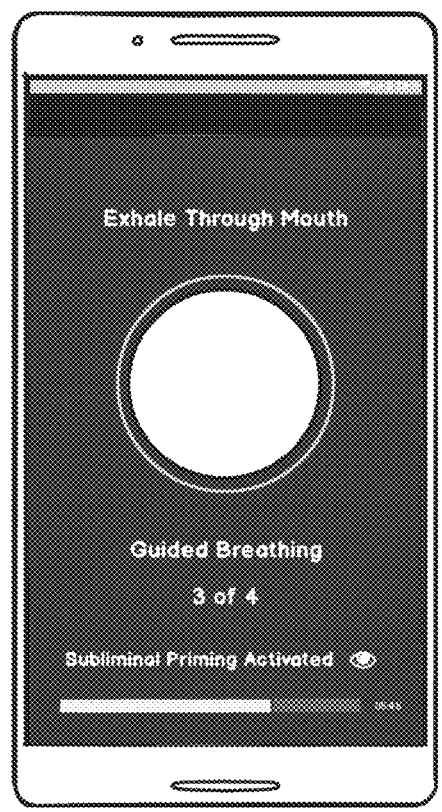
206
208
Software supporting various cognitive recovery protocols Software supporting cognitive and physiological recovery metrics FIG. 18A
FIG. 18B
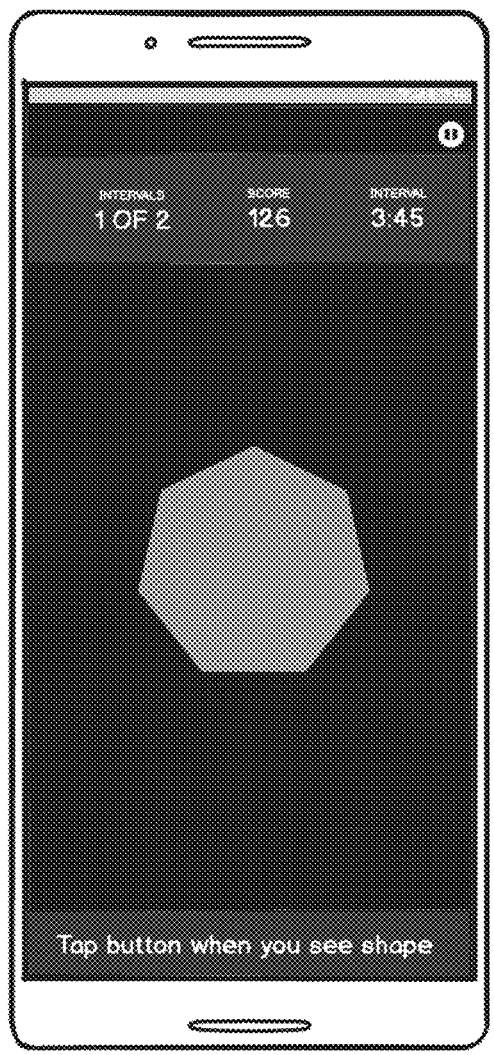
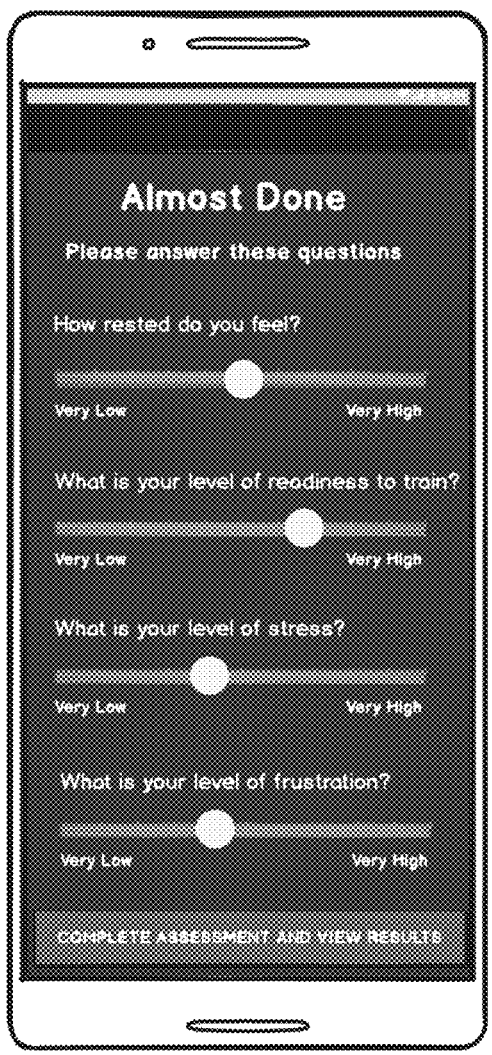
218
220
Software supporting cognitive fatigue self-assessment tests Flow chart summarizing selected operational details of the brain training software

ATHLETIC RECOVERY SYSTEM COMBINING COGNITIVE AND PHYSICAL ASSESSMENTS

CROSS-REFERENCE TO RELATED APPLICATIONS

This application is a continuation of U.S. patent application Ser. No. 16/799,458, filed on Feb. 24, 2020, entitled "ATHLETIC TRAINING SYSTEM COMBINING COGNITIVE TASKS WITH PHYSICAL TRAINING," which claims priority to and the benefit under 35 U.S.C. § 119(e) of U.S. Provisional Application Ser. No. 62/809,927, filed on Feb. 25, 2019, entitled "METHOD AND APPARATUS FOR IMPROVING ATHLETIC PERFORMANCE BY COMBINING COGNITIVE TASKS AND MOTIVATION TECHNIQUES WITH PHYSICAL TRAINING AT THE SAME TIME." The contents of these applications are incorporated herein by reference in their entirety.

TECHNICAL FIELD

This patent application relates generally to sports science, neuroscience and psychology, and more particularly to sports neuropsychology. This patent application relates more specifically to an athletic training system.

BACKGROUND

In the traditional physiological model of athletic training, the methodology to improve athletic performance and reduce the negative impacts of fatigue is grounded in the assertion that achieving the highest level of performance is limited by an individual's specific physiological, metabolic and biomechanical capacity. Therefore, this physiological model of athletic training has historically been focused on improving the individual's cardiorespiratory and anaerobic capacity by utilizing a variety of task-oriented physical conditioning techniques as a stimulus for physiological adaptation.

Research has been conducted on improving an athlete's overall performance as a result of cognitive tasks combined with physical training. See, Marcora, Samuele M. et al, "Mental fatigue impairs physical performance in humans", Journal of Applied Physiology, 2009, v. 106, n. 3, p. 857-864., Pageaux, B., Lepers, R., Dietz, K. C. et al, "Response inhibition impairs subsequent self-paced endurance performance", European Journal of Applied Physiology, 2014, v. 114, n. 5, p. 1095-1105., Martin, Kristy et al, "Superior Inhibitory Control and Resistance to Mental Fatigue in Professional Road Cyclists", PloS one, 2016, 11(7): e0159907.

Some of that research has been based on training the brain with inhibitory control tests during exercise to improve physical performance over time. See, Staiano, Walter et al, "A Randomized Controlled Trial of Brain Endurance Training (BET) to Reduce Fatigue During Endurance Exercise", paper presented at: American College of Sports Medicine (ACSM) Annual Meeting: San Diego, May 2015., Staiano, Walter et al, "Impact of 4-week Brain Endurance Training (BET) on Cognitive and Physical Performance in Professional Football Players: 3504 Board #192 June 1 8:00 AM-9:30 AM", Medicine & Science in Sports & Exercise, 2019, v. 51, n. 6, p. 964. Additionally, research has also confirmed that using motivational self-talk in conjunction with exercise enhances athletic performance. See, Blanchfield, Anthony et al, "Talking Yourself Out of Exhaustion: The Effects of Self-talk on Endurance Performance", Medicine & Science in Sports & Exercise, 2014, v. 46, n. 5, p. 998-1007.

Other research has shown that other cognitive recovery protocols may be used to reduce the effects of cognitive fatigue such as listening to Binaural beats, guided breathing, subliminal priming and other such protocols. See, Axelsen, J. L. et al, "On-the-Spot Binaural Beats and Mindfulness Reduces the Effect of Mental Fatigue", Journal of Cognitive Enhancement, 2020, OnlineFirst, 1-9.

Cognitive assessment for medical and psychological testing is known, but assessment techniques used for these purposes are poorly suited for conducting cognitive tasks during exercise. For example, prior art in these fields cannot be practically used by athletes during training because they require the use of a computer keypad or keyboard for the input of cognitive tasks. This type of solution is not practical or commercially viable as it would require the athlete to assume unnatural positions in order to interact with a keyboard and computer while performing the physical training with the cognitive task. Examples of such prior art within the medical, psychology and cognitive assessment fields include: U.S. Pat. No. 5,911,581, issued to Reynolds, et al. on Jun. 15, 1999; U.S. Pat. No. 6,416,472, issued to Cady, et al. on Jul. 9, 2002; U.S. Pat. No. 10,380,910, issued to Wu, et al. on Aug. 13, 2019; disclose various solutions conducting and measuring the results of cognitive tests using a computer and keypad or keyboard.

Within the sports domain prior art that efforts to combine sports training and cognitive function have one or more drawbacks. Examples of such prior attempts may be found in: U.S. Pat. No. 20090281450, issued to Reichow, et al. on Nov. 12, 2009; U.S. Pat. No. 10,478,698, issued to Tinjust on Nov. 19, 2019. These references disclose systems used for cognitive tasks during physical training. However, the inventors have recognized that the disclosed approaches suffer from several disadvantages for improving athletic performance. For example, they do not contemplate the neuropsychological model of cognitive and physical training and therefore do not incorporate cognitive tasks that, when combined with physical exercise, are effective at inducing mental fatigue and creating a cognitive performance adaptation over time. Additionally, these references do not provide ergonomic input devices for cognitive testing that can be easily adapted to a plurality of sports without compromising range of motion, eye-hand coordination, athletic form or safety. Further, they do not contemplate other cognitive solutions to improve performance, such as incorporating cognitive recovery protocols and psychological-based motivation techniques.

BRIEF SUMMARY

Inventive concepts as described herein may be embodied as an athletic training system for improving athletic performance by combining cognitive tasks with physical training. The system may comprise a user input device configured to send messages to a computer and a computer configured to receive messages from the input device corresponding to cognitive tasks. The computer may comprise at least one processor, a user interface; and computer-storage medium storing computer executable instructions that, when executed by the at least one processor, conduct, via the user interface display of the computer and the user input device, a cognitive training session. The computer-executable instructions may comprise a self-calibration component configured to record an athlete's cognitive and physical output;

a first interface component configured to receive user input selecting from a plurality of cognitive and physical workout options; a second interface component configured to provide output guiding a user through both cognitive and physical tasks within the same workout; a self-rating component configured to assess cognitive and physical fatigue based on one or more inputs; a third interface component configured to provide real-time physical and cognitive metrics based on an evaluation of the athlete's performance; an evaluation component configured to provide a summary of the athlete's cognitive and physical training performance results.

In another aspect, the inventive concepts as described herein may be embodied as a method of operating an athletic training system for providing a plurality of cognitive and physical recovery protocols. The method may comprise receiving through an interface user input selecting from a plurality of cognitive and physical recovery options; presenting an interface that combines multiple recovery protocols in a single interface; capturing at least one physiological metric as part of a recovery evaluation process; assessing level of cognitive and physical stress of a user based on input provided by the user; and providing a summary of the user's cognitive and physical recovery results.

In another aspect, the inventive concepts as described herein may be embodied as a method of operating an athletic training system for improving athletic performance by combining cognitive tasks with physical training. The method may comprise: presenting through a user interface cognitive tasks for a user to perform; and during a training session, adapting difficulty of the cognitive tasks.

The foregoing any other techniques as described herein may be used separately or together in a combination of any two or more of those techniques.

BRIEF DESCRIPTION OF DRAWINGS

FIG. 1A illustrates an exemplary embodiment of a tactile-based input apparatus that includes waterproof, ergonomic, pressure sensitive buttons that attach to the body or training machine.

FIG. 9 illustrates an exemplary embodiment of a user interface supporting real time physiological and cognitive output metrics captured and displayed during training on a portable computing device such as a smartphone or desktop computer.

FIG. 13 illustrates an exemplary embodiment of a user interface supporting lookup tables designed to compare an athlete's self-rated performance with physiological and cognitive output measurements captured during training using a computing device such as a smartphone or desktop computer.

FIG. 16A illustrates an exemplary embodiment of a user interface supporting the integration of various cognitive recovery protocols for improving motivation and physical and mental recovery.

FIG. 16B illustrates an exemplary embodiment of a user interface supporting the integration of various cognitive recovery protocols for improving motivation and physical and mental recovery.

FIG. 18A illustrates an exemplary embodiment of a user interface supporting a cognitive fatigue self-assessment system to be completed regularly by athletes to determine their current level of mental fatigue compared to their baseline.

FIG. 18B illustrates an exemplary embodiment of a user interface supporting a cognitive fatigue self-assessment system to be completed regularly by athletes to determine their current level of mental fatigue compared to their baseline.

DETAILED DESCRIPTION

Figure 1B:
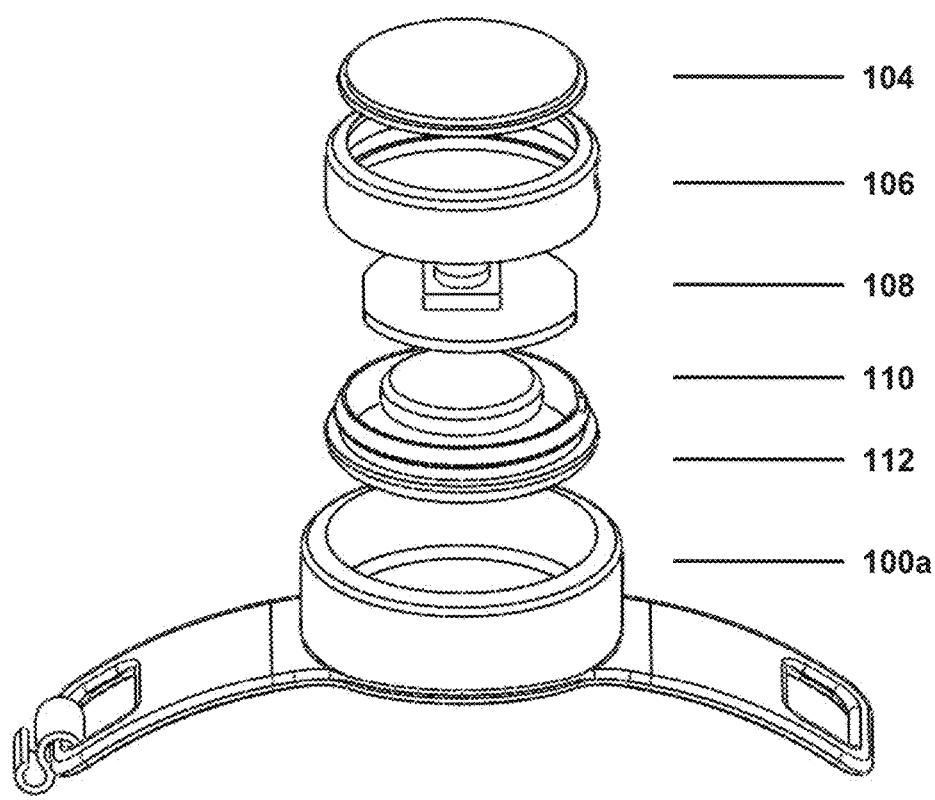
FIG. 1B illustrates an exemplary embodiment of a tactile-based input apparatus with button and strap in exploded view.

The inventors have recognized and appreciated designs for an athletic training system, including apparatus and software, that aids athletes in enhancing their physical performance by incorporating a neuropsychological model for cognitive brain training in conjunction with physical exercise.

In some embodiments, the apparatus and/or software may be based on cognitive brain training through tasks that have been shown to activate the area of the brain associated with mental fatigue known as the anterior cingulate cortex (ACC) found within the prefrontal cortex. In some embodiments, the neuropsychological cognitive tasks that are used include the Stroop Task, Psychomotor Vigilance Task (PVT), Go/No Go Task, Continuous Performance Task (CPT), Stop Signal Task (SST) and/or other similar tasks. One or more such tasks, which require a continued level of focus and inhibitory control creating a mentally fatigued state in the athlete, may be performed in conjunction with physical exercise in order to create adaptation and improve resilience to mental fatigue with continued practice by the athlete.

In contrast to known research set-ups, an athletic training enhancement system as described herein may be practical and commercially viable as it does not require an athlete to assume unnatural positions in order to interact with computer input and output devices while performing the physical task. Rather, in accordance with some embodiments, an ergonomic input device may be used for cognitive tasks in conjunction with physical exercise across a plurality of different sports without compromising range of motion, eye-hand or athletic form. Techniques as described herein are amenable to implementation so as to be easily portable or extensible to different sports and physical movement modalities. In some embodiments, the disclosed techniques may be extended to sports that require both a free range of motion and eye-hand coordination, such as cycling, strength training, rowing, swimming, running, rugby and basketball.

In some embodiments, a simple and portable user interface device, such as a button or other sensor that detects movement of a portion of a user's body, may interface with a computer executing software that processes inputs and generates outputs to implement an athletic training system. The user interface may be integrated with a support structure so that it may be worn by a user or attached to a piece of athletic equipment. A button, for example, may be attached to a strap, which a user may hold or may be mounted to equipment, such as a bicycle handlebar. Alternatively or additionally, a sensor may be integrated into an item worn by a user, such as a glove or other piece of clothing or a wrist band.

In some embodiment's, a training enhancement system may alternatively or additionally provide user stimulus based on motivational techniques and cognitive recovery protocols, which may also be used in conjunction with physical training.

In some embodiments, a training enhancement system may perform a cognitive fatigue assessment to help the athlete calibrate their level of daily training activity.

I. Computing Systems

The systems and methods described herein rely on a variety of computer systems, networks and/or digital devices for operation. In order to fully appreciate how the system operates, an understanding of suitable computing devices and systems is useful. The computing devices, systems and methods disclosed herein are enabled as a result of application via a suitable computing device (including without limitation mobile devices such as smartphones and tablets). In at least some configurations, a user executes a browser on a computer to view digital content items on a display associated with the computer. Digital content may be stored or generated on the computer or may be accessed from a remote location. For example, a computer can obtain content by connecting to a front end server via a network, which is typically the Internet, but can also be any network, including but not limited to a mobile, wired or wireless network, a private network, or a virtual or ad hoc private network. As will be understood very large numbers (e.g., millions) of users are supported and can be in communication with the website at any time. The user may utilize a variety of different computing devices. Examples of user devices include, but are not limited to, personal computers, digital assistants, personal digital assistants, cellular phones, mobile phones, smart phones, tablets or laptop computers. The browser can include any application that allows users to access web pages on the World Wide Web. Suitable applications include, but are not limited to, Chrome®, Brave®, Firefox®, Microsoft Edge®, Apple®, Safari or any application capable of or adaptable to allowing access to web pages on the World Wide Web. Primarily, a user may download an app, e.g., onto the user's portable computing device, in order to perform brain training and mental recovery tasks on the user's hand held device or other user computing device.

A computer may have one or more processors that may execute computer-executable instructions stored in non-transitory computer-readable storage media, such as volatile or non-volatile memory. A computer may have one or more input devices, such as a keypad or touch screen for receiving tactile input. The computer may have a sound input, such as a microphone, for receiving audible input, such as speech that may be recognized as commands. The computer alternatively or additionally may have a camera to receive input in visual form.

Further, the computer may have interfaces, such as a wireless interface, USB port or other I/O port, that may be connected to sensors or other input devices. For example, one or more sensors, such as a pulse sensor, sweat sensor or other sensor that provides an output indicative of physical activity or exertion may be wirelessly coupled to a computer.

A computer may have one or more output devices, such as a display screen or speaker. The input and output devices may be integrated into one physical unit or may be coupled to a unit via wires or wireless connections.

These components integrated into a or coupled to a computer may be accessed by programming of the athletic training system to provide output to or collect input from a user of the system as described further herein.

II. Cognitive Brain Training

Described herein is a training system for athletes and other users with both an apparatus and software-based methodology for cognitive brain training to be done in conjunction with physical exercise. The system may have one or more components that interact with a user to reduce the effects of mental and physical fatigue and improve overall athletic performance. These components may drive interaction with the user both before, during and after a training session. During a physical training session, the system may guide the user in performing cognitive tasks that train the user's brain to resist cognitive fatigue. The system may also collect inputs about the user's physical exertion and performance as well as cognitive fatigue, for adapting guidance provided on physical exertion or adapting cognitive training tasks. The system may also render motivational content to the user.

Before a physical training session, the system may collect input from the user, including on phrases that the user considers motivational. Inputs may also be collected for calibration of the system.

After a training session, the system may collect inputs indicative of user cognitive or physical fatigue, including through self-assessment inputs, and may output cognitive and physical metrics associated with the training session.

Figure 1C:
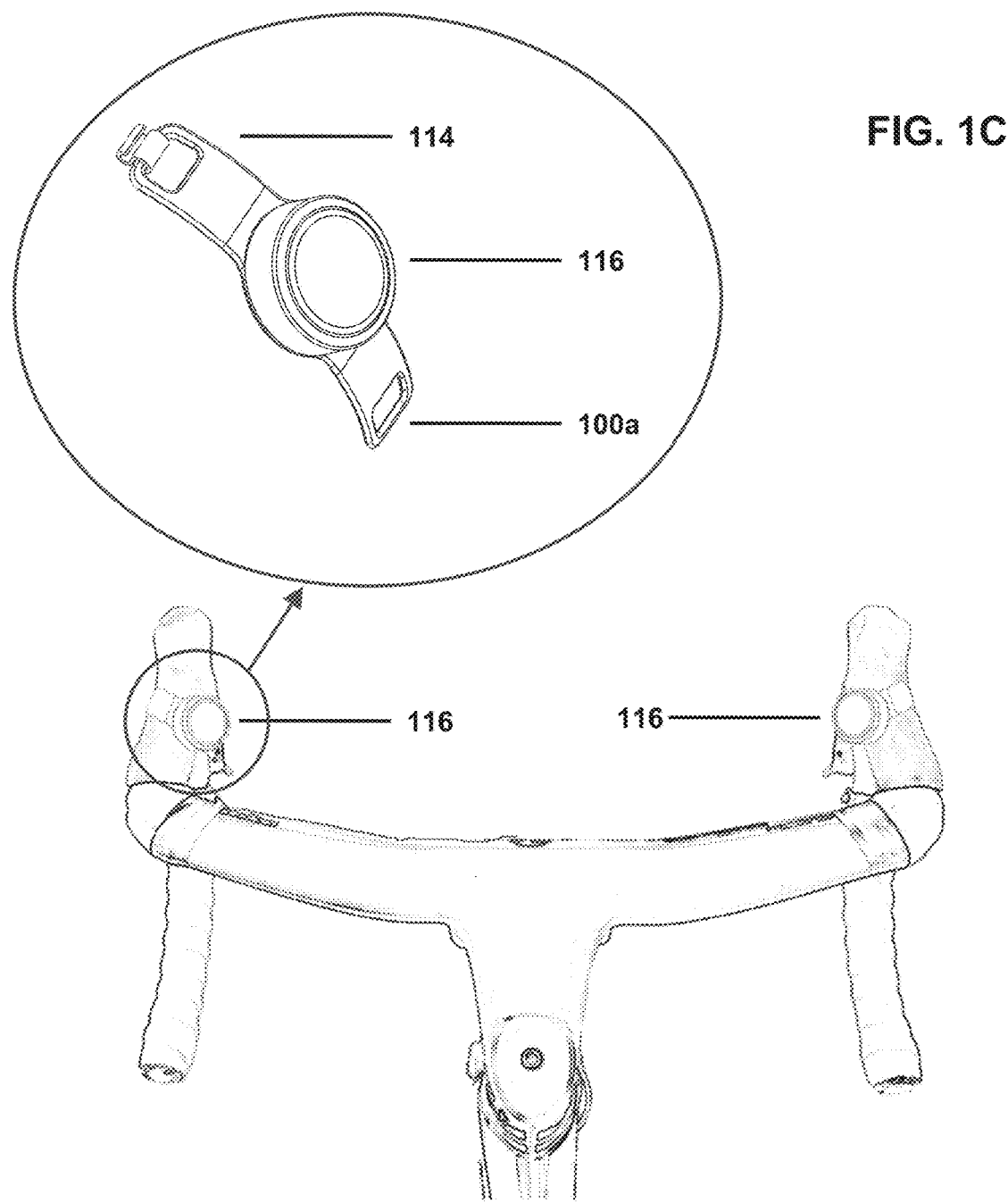
FIG. 1C illustrates an exemplary embodiment of a tactile-based input apparatus with buttons and straps to be attached to bicycle handlebars.
Figure 1D:
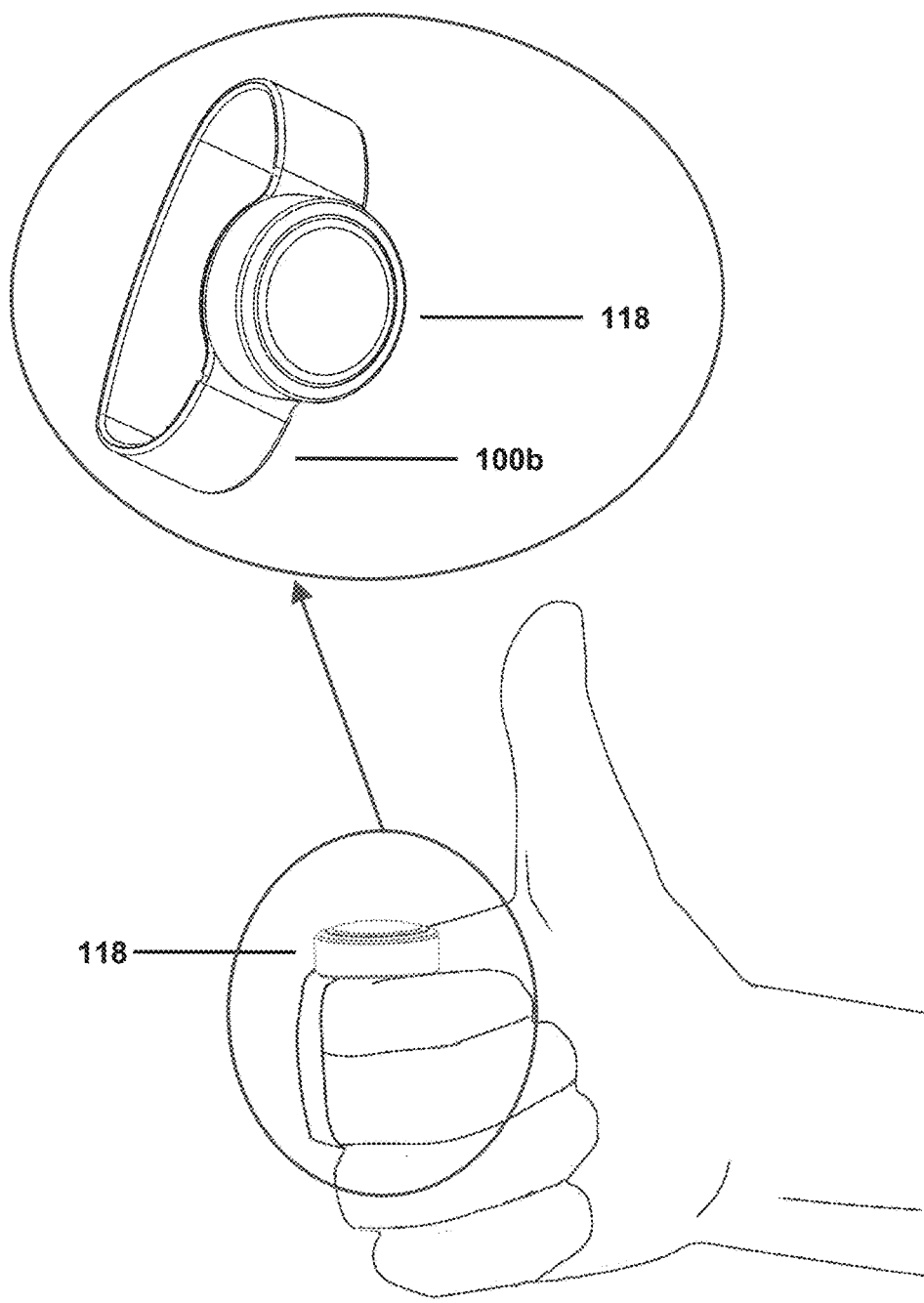
FIG. 1D illustrates an exemplary embodiment of a tactile-based input apparatus with buttons and straps to be held in the hands.
Figure 4:
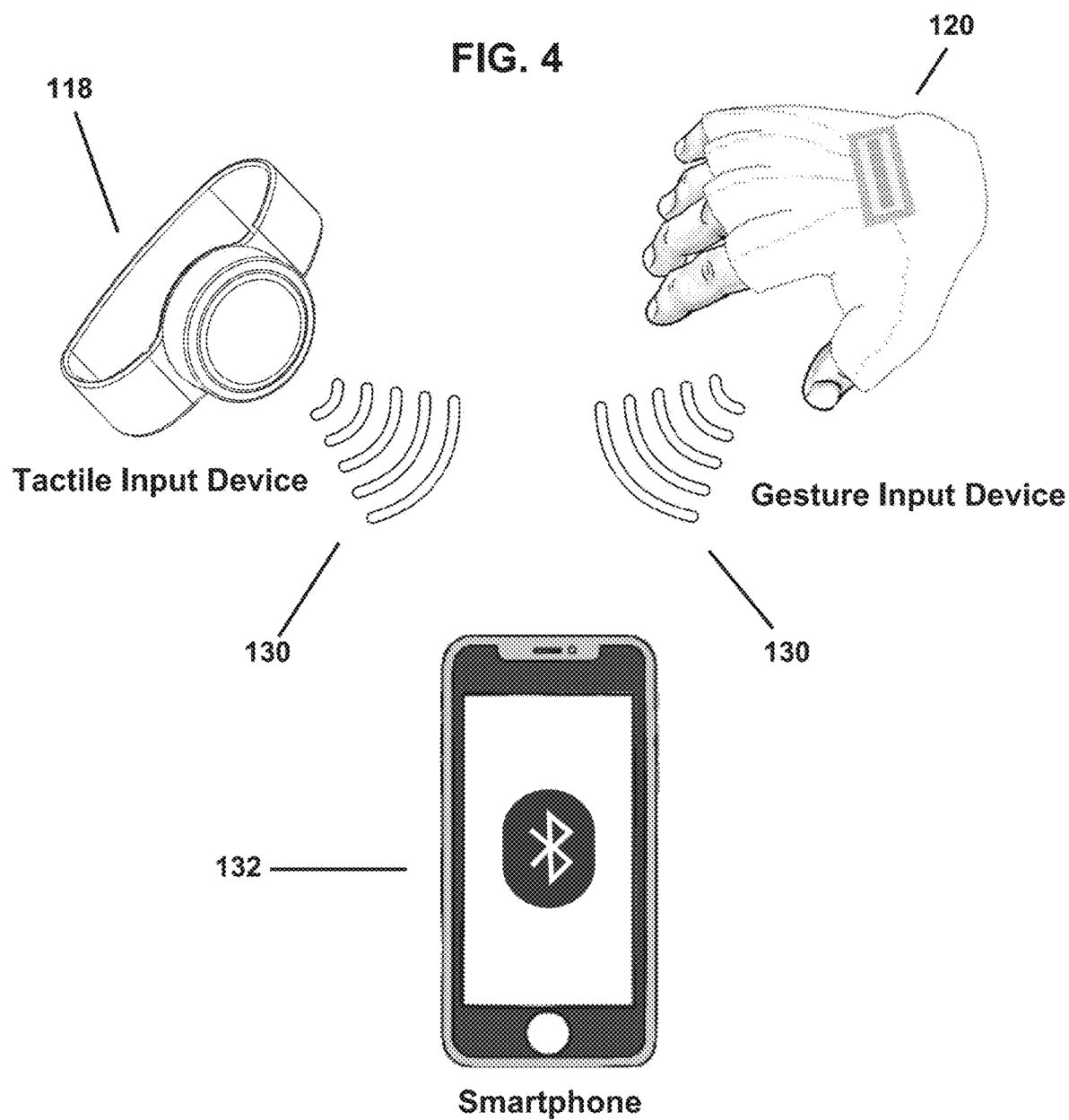
FIG. 4 illustrates an exemplary embodiment of a software supporting the input apparatus devices to connect wirelessly with a portable computing device such as a smartphone or desktop computer.

The following is a detailed description of an exemplary embodiment of such an athletic training system and its use by the athlete inclusive of all of the components described here in. First an athlete turns on or enables the input device to be used during cognitive training in FIGS. 1A-D, 2, 3. In the case of a tactile-based input apparatus embodiment in FIGS. 1A-D, the athlete may attach pressure sensitive buttons 102 and straps 100a, to a training machine such as on the handlebars of an indoor bicycle trainer 116 in FIG. 1C by attaching the tactile apparatus with a clip 114 and strap 100a or by attaching the tactile-based input apparatus to their hands 118 in FIG. 1D with pressure sensitive buttons 102 and straps 100b. The tactile-based apparatus device in FIG. 1B is made up of a large button surface area cap 104, a waterproof top enclosure 106 that covers the printed circuit board (PCB) 108, a battery 110 and a waterproof bottom enclosure for the PCB 112, and a strap 100a for attaching the button to a training machine. In FIG. 4 the tactile-based button 118 then sends wireless signals 130 to a portable computing device such as a smartphone 132 or desktop computer running a custom application.

Figure 2:
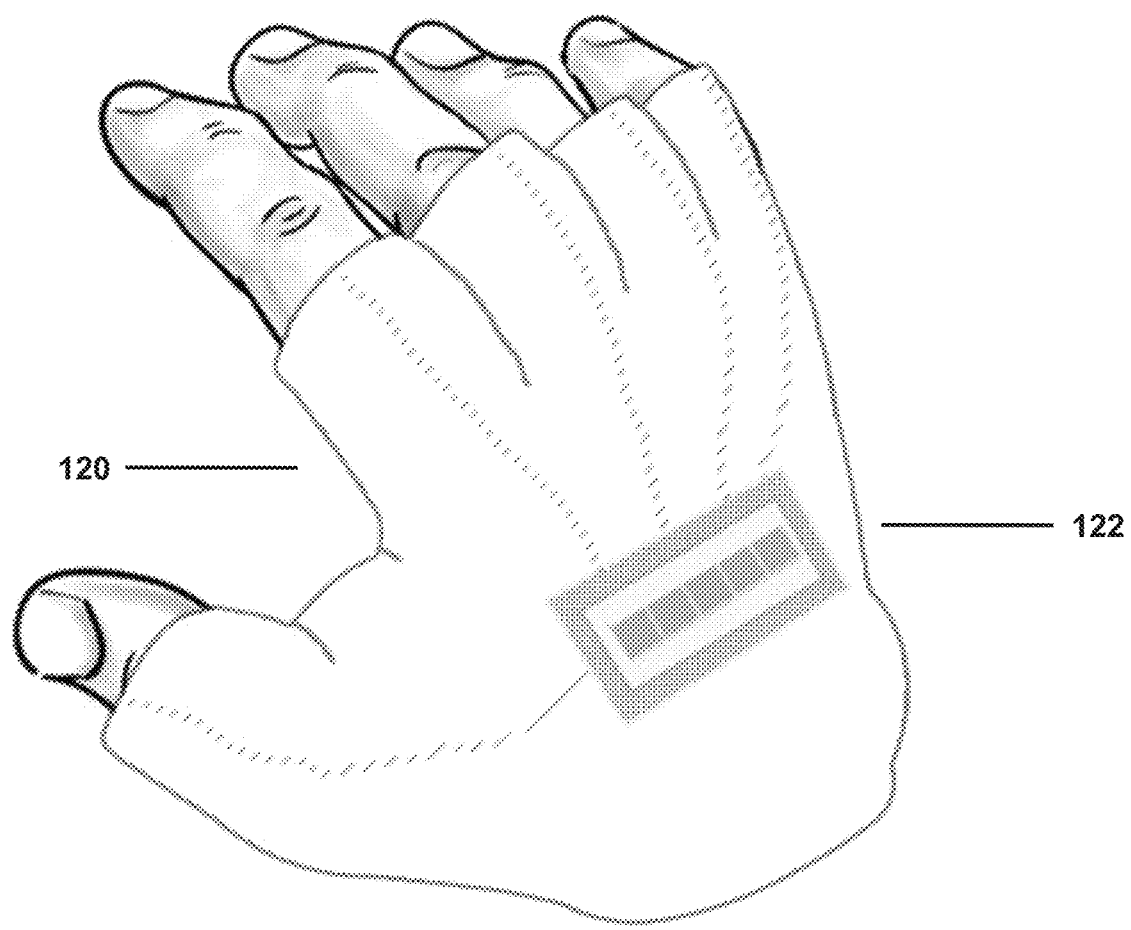
FIG. 2 Illustrates an exemplary embodiment of a gesture-based input apparatus version that includes waterproof, ergonomic sensors attached to the body or training machine.
Figure 3:
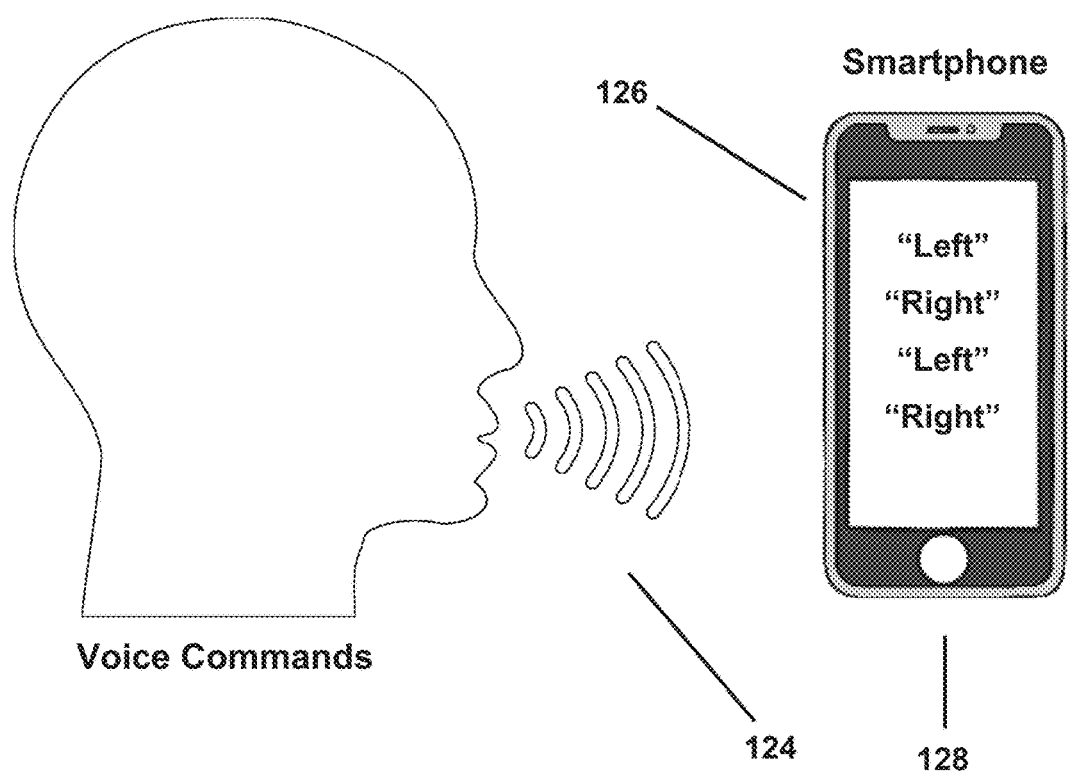
FIG. 3 illustrates an exemplary embodiment of a software supporting a voice-based input version to capture commands from an athlete using a portable computing device such as a smartphone or desktop computer.

In additional embodiments, such as the gesture-based input apparatus version 120 in FIG. 2, the athlete attaches the gesture device 120 to the hands with motion sensors 122 integrated into a glove, strap or other hand-held device. In FIG. 4 the gesture-based apparatus 120 then sends wireless signals interpreted by software 130 running on a portable computing device such as a smartphone 132 or desktop computer. In the case of the voice-based input version of the embodiment in FIG. 3, the athlete uses voice commands 124 or other spoken inputs that are interpreted by the software 126 running on a portable computing device such as a desktop computer or smartphone and ensures that the portable computing device's microphone is enabled 128.

Figure 5:
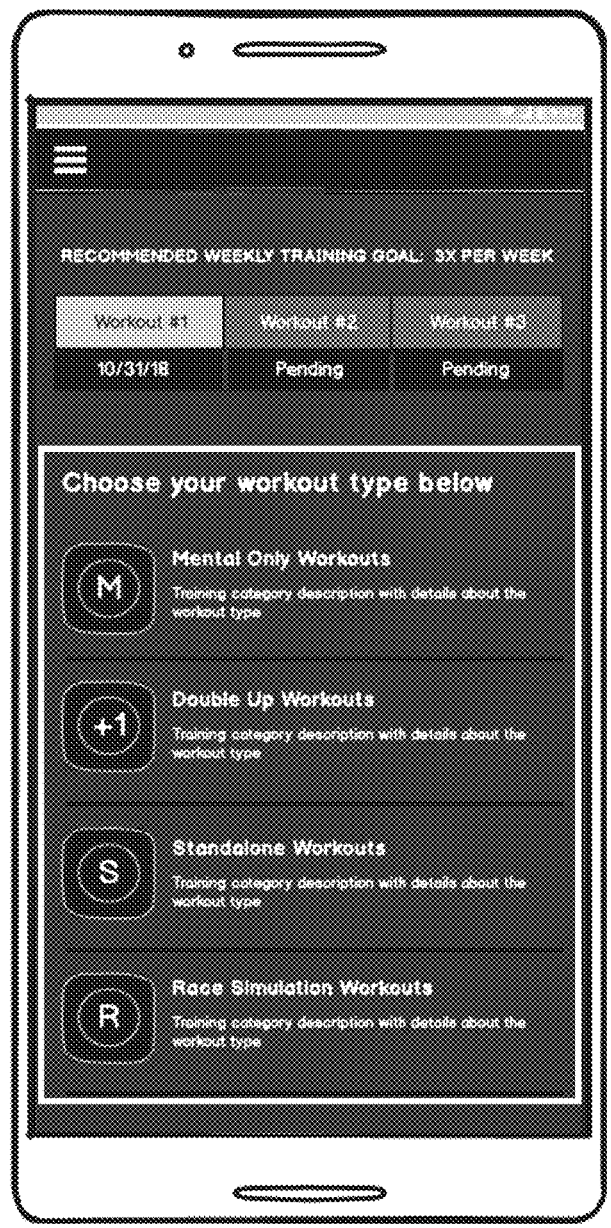
FIG. 5 illustrates an exemplary embodiment of a user interface supporting the selection, delivery and recording of various cognitive and physical workout programs.
Figure 6:
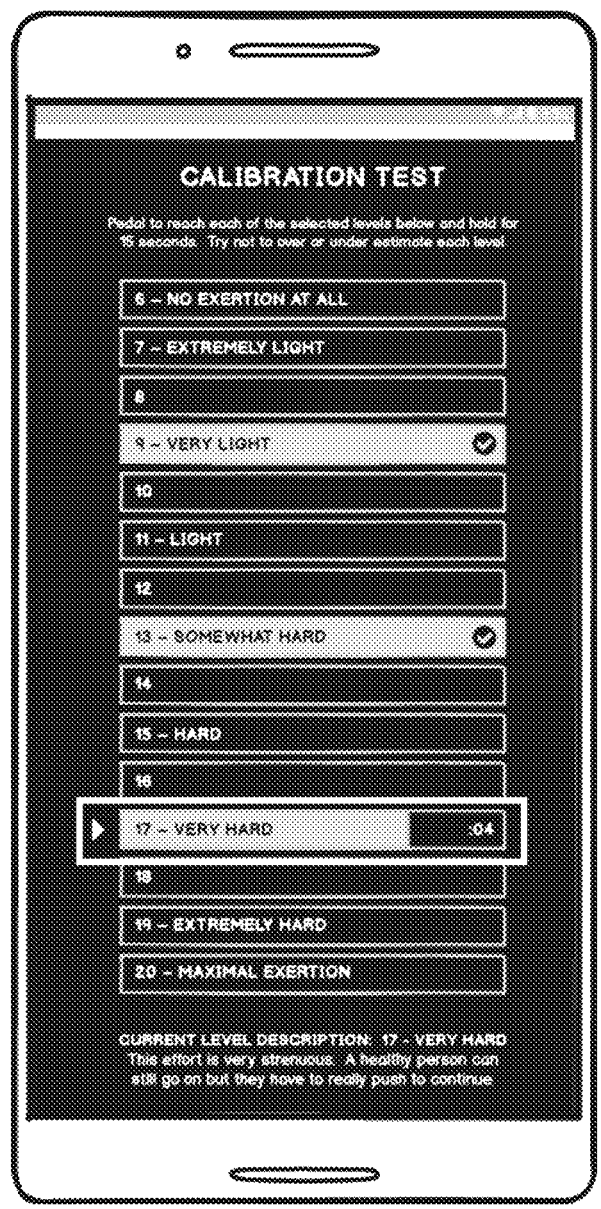
FIG. 6 illustrates an exemplary embodiment of a user interface supporting a self-rating calibration system to be completed by athletes at the start of the workout using a computing device such as a smartphone or desktop computer, shown here executing on a portable device mounted on exercise equipment.

After either the tactile button (FIGS. 1A-D), the gesture (FIG. 2) or the voice-based (FIG. 3) input device is enabled and (where applicable) connected to the portable computing device, the athlete selects a workout in FIG. 5 from one of the choices available 134 from within the software application and the workout begins. At the start of the workout, the athlete may be asked to perform a calibration test (FIG. 6) that records the athlete's perceived level of effort. Perceived effort may be represented using a point scale system 136 that measures the athlete's rating of perceived exertion (RPE) at different physical output levels such as "17—Very Hard" 138 where the athlete exerts physical effort to meet that perceived level of effort indicated on the scale 136. As the athlete completes the calibration test, standard physiological measures from this test are saved into lookup tables for further analysis (FIG. 13) such as power measured in watts for the functional threshold power (FTP) lookup table 182 and heart rate measured in beats per minute for the lactate threshold heart rate (LTHR) lookup table 186. In this way, the user's perceived physical effort may be correlated with measured values before, during and after the workout in order to track cognitive and physiological performance over time. Additionally, these calibrated measures may be used during a training session to adapt the level of difficulty automatically for various cognitive tasks based on the user's perceived level of effort. For example, if the user's rating of perceived exertion becomes reduced, even with the same amount of physical and cognitive stimuli as prior workouts, this may indicate a positive adaptation to the cognitive tasks, and the task difficultly may automatically increase or decrease in length, complexity or other stimuli depending upon the training goal or workout selected by the user.

Figure 7:
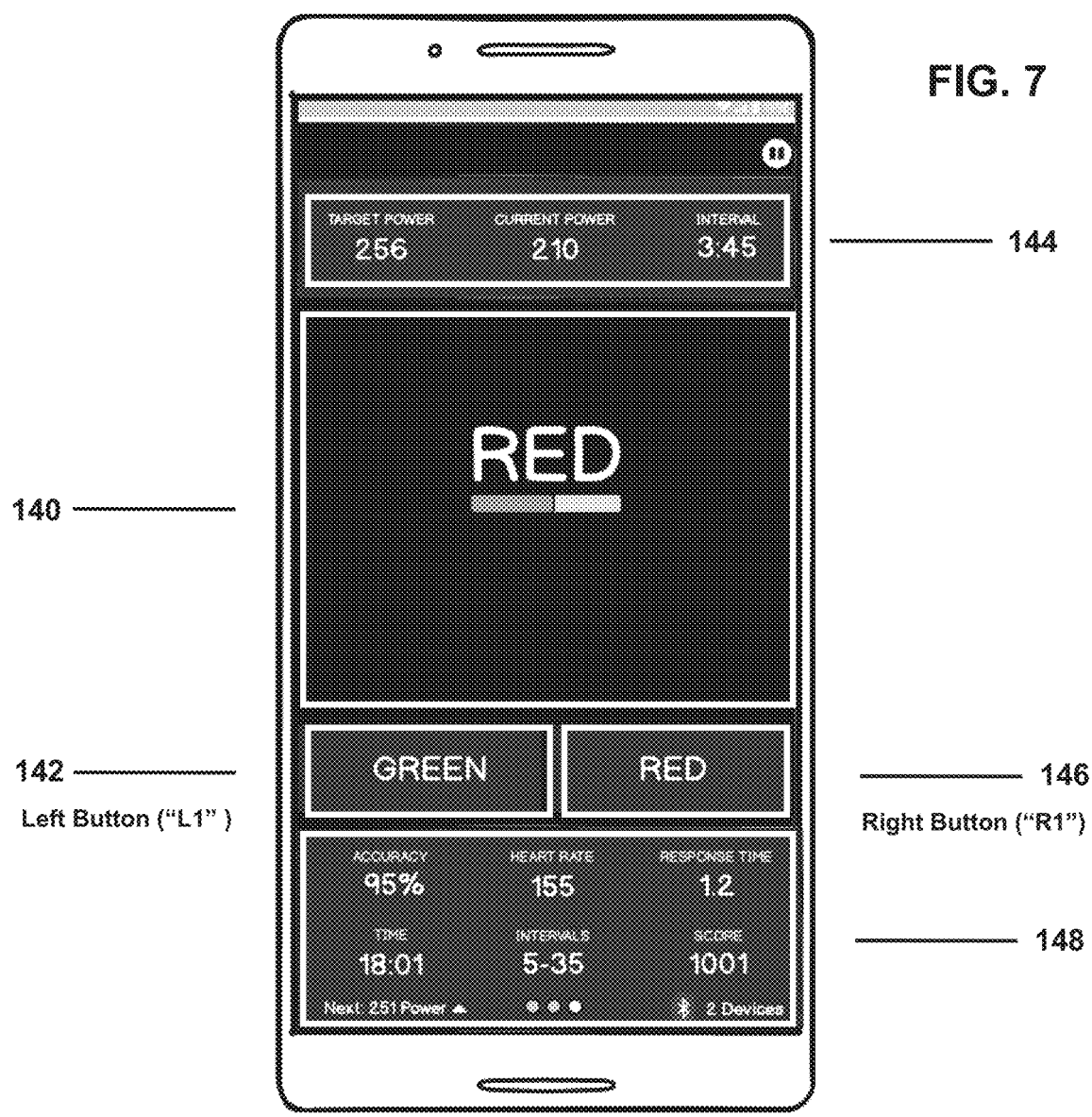
FIG. 7 illustrates an exemplary embodiment of a user interface supporting cognitive training interfaces displayed on a portable computing device such as a smartphone or desktop computer.

During the workout in FIG. 7, the athlete is presented with different cognitive training interfaces based on their training goals featuring various neuropsychological tasks that target specific areas of the brain and brain pathways helpful for overcoming cognitive fatigue and improving athletic performance. For instance, the neuropsychological task known as the Stroop Task 140, is an established task for measuring response inhibition and requires the user to have the ability to overcome automatic tendencies in order to respond correctly to each task. For example, in a Stroop task the user will be presented with a color word (e.g., "red", "green" or other colors) that is presented in one of multiple ink colors (e.g., green, red or other colors). Users are instructed to respond based upon the ink color of the word, not the identity of the word itself. When the color and the word are congruent (e.g., "red" in red ink), the natural tendency to read the word facilitates performance, resulting in fast and accurate responses. When the color and the word are incongruent (e.g., "red" in green ink), the strong, natural tendency to read the word must be overcome to respond to the correct ink color. Similarly, the Stop Signal Task (SST) is also an established task for measuring response inhibition and consists of a "go stimuli" such as a series of left or right arrows that users are instructed to respond quickly to every time they are displayed on the cognitive testing interface. On a subset of the tasks, the go stimulus is followed, after a variable delay, by a "stop signal" such as an audible beep or upward pointing arrow, to which users are instructed to inhibit their response. In other neuropsychological tasks such as the Psychomotor Vigilance Task (PVT), Go/No Go Task, Continuous Performance Task (CPT) users must maintain sustained attention to a specific set of stimuli such as identifying certain objects that appear and disappear on the cognitive testing interface as quickly as possible which measure the user's reaction time, alertness, level of cognitive fatigue and decision making ability. These different neuropsychological tasks are performed in conjunction with physical exercise in order to improve cognitive and physical performance over time.

In some embodiments, the difficulty of the cognitive tasks may be adapted during a training session. For example, the level of difficulty of the cognitive task may be increased by increasing the level of complexity of the task questions, reducing the amount of time allowed for each question and/or increasing a target score needed to successfully complete a given cognitive task. In some embodiments, cognitive difficulty may be adapted based on a user's perceived level of effort, which may be determined from the calibrated measures of physical exertion. For example, as a user increases their physical exertion such that their perceived level of exertion increases, the cognitive difficulty of the tasks may be increased.

In some embodiments, a control function relating perceived level of effort to cognitive difficulty may be linear. In some embodiments, the level of cognitive difficulty may increase step wise as various levels of perceived effort are reached, but there may nonetheless be a general trend that level of cognitive difficulty increases in relation to perceived exertion. In other embodiments, the control function may be non-linear or may be linear over a range of perceived exertion.

Moreover, the control function may be based on parameters in addition to perceived level of effort. Training goals input by a user may be used in the function. For a user that has specified a higher goal, for example, the increase in cognitive difficulty may be greater for each unity of increase in perceived exertion. Alternatively or additionally, time may be a parameter. For example, the duration of planned workout may impact the amount of increase in cognitive difficulty, with more increase for shorter workouts or where there is a shorter time remaining in the planned workout.

As an example of another parameter that may impact the control function, the user's sense cognitive fatigue may be used in setting the level of cognitive difficulty. As the user's cognitive fatigue increases, the level of cognitive difficulty may be increase at a slower rate or may be decreased in some scenarios.

Further, in some embodiments, the level of cognitive difficulty may also be calibrated based on measurement taken before, during or after an exercise session. As described herein, the system may prompt a user to provide inputs serving as an assessment. That assessment may include a perceived level of cognitive difficulty. During or after presenting one or more cognitive tasks to the user, the system may prompt the user to provide an assessment of perceived difficulty of the task. This assessment may be performed under different conditions to provide different levels of mental challenge such that the variations in the task may be equated to a perceived level of difficulty for the user. Upon determining, during a training session a desired level of cognitive difficulty, the appropriate task and conditions of that task corresponding to that level of perceived cognitive difficulty may be selected.

These tasks may be configured to be performed by a user with a simple input device. For example, the athlete tap the tactile buttons when using an input device as pictured in FIGS. 1A-D, make gestures when using an input device as pictured in FIG. 2, or speak voice commands when using an input device as pictured in FIG. 3 to input answers to cognitive task prompts. The prompts may be questions as indicated in FIG. 7. These responses may be received and processed by a custom application through a series of coded messages transmitted wirelessly 130 (FIG. 4) or by voice inputs 124 (FIG. 3) which are then interpreted by the software 150 (FIG. 8), 126 (FIG. 3) in order to be translated into correct and incorrect answers for the cognitive tasks. The coded messages may take the form of alphanumeric values or phrases that correspond to answers to cognitive questions such as "R1" and "L1" 150 (FIG. 8) or "right" and "left" 126 (FIG. 3) that can be interpreted by the software on the portable computing device to mean "Go Right" input for "R1" or "right" and the "Go Left" input for "L1" or "left" which also correspond to answer buttons on the left 142 and the right 146 side of the cognitive testing interface in FIG. 7.

While the athlete is performing cognitive tasks they are also given prompts by the software, which may be provided through a system output device such as a display 144 (FIG. 7) and audio and visual prompts that appear in order to notify the athlete when their thresholds are above or below target physiological output goals such as maintaining a specific heart rate or maintaining a specific power output measured in watts.

Figure 8:
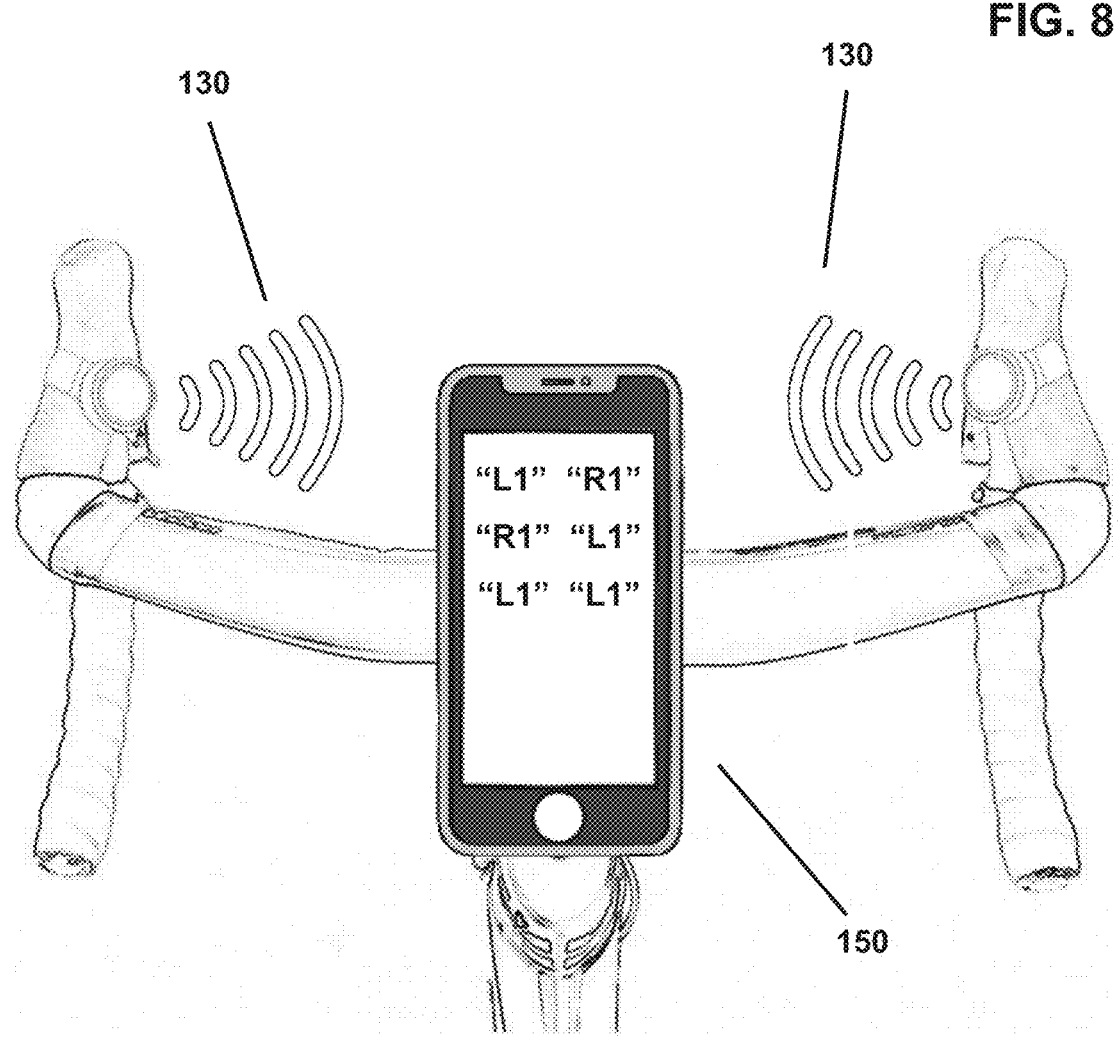
FIG. 8 illustrates an exemplary embodiment of a user interface supporting the reception and translation of coded messages sent wirelessly from the input apparatus device to a portable computing device running the custom application.

The prompts may be presented in a format that a user may observe while performing a physical task. The notifications may, for example, be large colored areas or simple graphical symbols, such as progress bars or dials. The notifications may be presented through a display on a portable device that is mounted in a location that the user can observe while performing physical tasks. In the example of FIG. 8, a portable computing device, such as a smartphone is mounted on the handlebars of a bicycle used for training. The smartphone may execute the software that generates notifications and processes responses to them. In some embodiments, the portable electronic device may also serve as an input device, as a user may provide input through a touch interface of the display. However, it is not a requirement that the portable computer device be in the user's field of view as in some embodiments, notifications may be provided in other ways, such as audibly, through vibration of the portable computing device, or wirelessly to a speaker or other output device.

In addition to the display and audio and visual alerts, the physiological target goals may also be represented visually in the form of a real-time progress bar 152 (FIG. 9) that is integrated into the cognitive task questions 140 (FIG. 7) so that the athlete can maintain focus on both their physiological target goals as well as the cognitive tasks at the same time. For example, in the case of the Stroop cognitive task the progress bar will be attached to the bottom of the primary color word that appears on the screen e.g. "PURPLE" 152. In other cognitive tasks the progress bar may be adapted to be attached to various shapes or symbols appearing at different locations of the cognitive testing screen so that the athlete can easily keep track of their physiological target goals while still focusing on the cognitive task questions. The progress bar 152 (FIG. 9) visually represents the user's current physiological output percentage compared against their target goals. For example, at rest the progress bar is "empty" with no highlight color on any portion of the bar 154 showing only a gray background on the bar which indicates that there is no current physiological output being generated by the athlete. When the progress bar is extended to 50% of the allowable space by a highlighted color on the bar 156 this indicates to the athlete that their current output is only 50% of their target physiological goal. As the athlete continues to increase their physiological output in order to match the target goal the highlighted color portion of the progress bar will continue to extend in length until it reaches 100% of the allowable space 158 indicating that the athlete has met the target goal and should maintain their current physiological output level in order to ensure that the progress bar remains fully extended (FIG. 9). If the athlete exceeds the target goal of over 100% the progress bar will highlight in a different color on the far right edge of the bar 160 indicating that the athlete should reduce their physiological output in order to achieve the target goal of 100% (FIG. 9).

Figure 10:
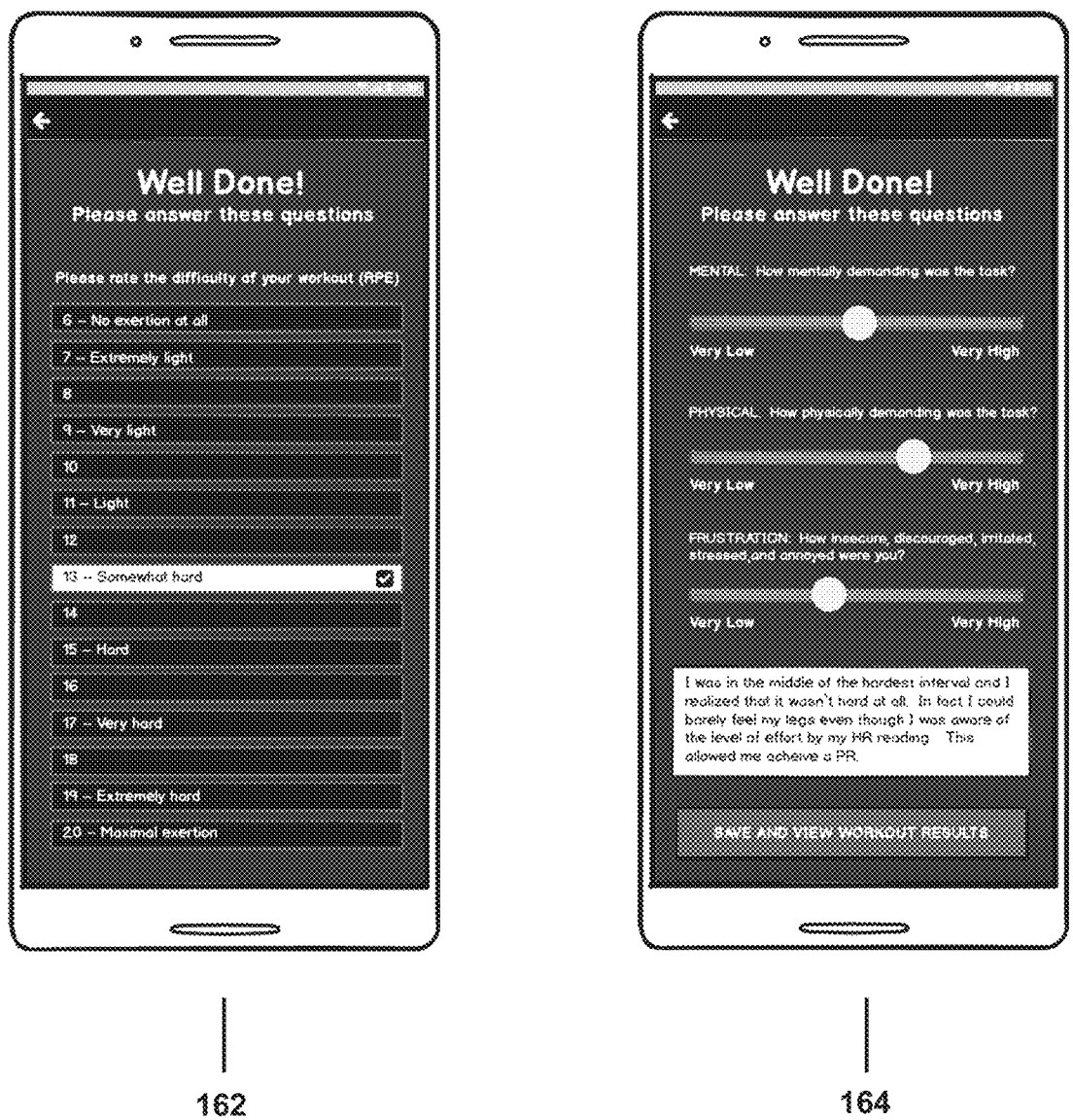
FIG. 10 illustrates an exemplary embodiment of a user interface supporting a quantitative and qualitative self-rating system to be completed by athletes at the end of the workout using a computing device such as a smartphone or desktop computer.

Upon the completion of the workout (FIG. 10) the athlete is asked to answer a series of quantitative and qualitative questions to self-rate their overall performance including their rating of perceived exertion (RPE) for the workout 162 and several psychological questions 164 related to how mentally and physically demanding the workout was for them. The cognitive training software then uses a series of metrics, formulas and algorithms to combine the athlete's self-rated metrics 162, 164 (FIG. 10) with the real-time cognitive and physiological output metrics 148 (FIG. 7) to provide reports that summarize the athlete's performance for each workout (FIG. 11).

Figure 11:
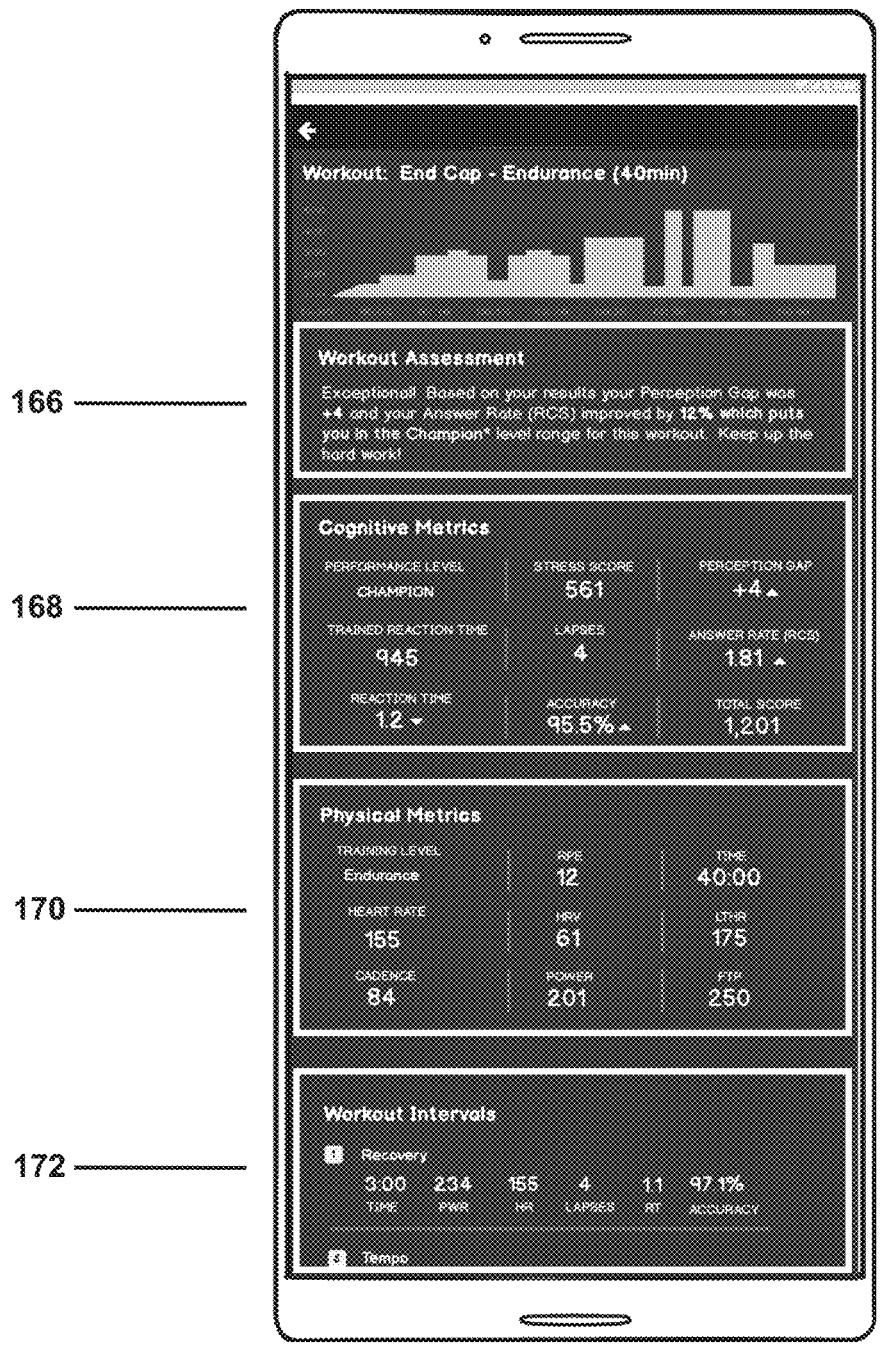
FIG. 11 illustrates an exemplary embodiment of a user interface supporting cognitive and physiological performance metrics, formulas and algorithms to be recorded and calculated using a computing device such as a smartphone or desktop computer.

FIG. 11 shows the end of workout report that includes the athlete's workout assessment 166, cognitive metrics 168, physical metrics 170 and workout intervals 172. The sections in FIG. 11, display critical cognitive and physical metrics from the workout. Cognitive metrics may be computed based on user responses received during cognitive tasks, such as total score 168 measured by the total number of correct answers during all cognitive tasks, reaction time 168 measured by the average length of time to respond to each of the cognitive questions correctly, accuracy 168 measured by the percentage of correct answers per interval and overall, answer rate (RCS) 168 measured by the athlete's total correct answers (per workout) divided by the sum of their reaction time, lapses 168 measured by counting the total number of slower than average responses to the brain training tasks. These cognitive metrics may be used to adapt the level of difficultly of cognitive tasks during subsequent workouts by automatically increasing or decreasing the level of complexity of the task questions, increasing or reducing the amount of time allowed for each question and increasing or decreasing the target score needed to successfully complete a given cognitive task. For example, if the athlete's answer rate (RCS) is consistently better than their baseline percentage for more than a predefined number of prior workouts then the difficultly level of the athlete's cognitive tasks in their next workout will be increased in order to ensure that they are receiving the right amount of cognitive stimuli to continually improve. Additionally, within the workout assessment 166 the cognitive metrics may be used to recommend additional training or recovery sessions based on the athlete's performance. For example, if the athlete's perception gap score is significantly lower in terms of performance from their baseline percentage in a given workout then the workout assessment may include a recommendation to temporarily discontinue cognitive training and instead increase the number of cognitive recovery sessions in order to rest and recover before resuming cognitive training.

Physical metrics may be computed based on sensor inputs received during a training session, such as heart rate (average) 170 measured by average beats per minute, heart rate variability (HRV) 170 measured by the time variance in between each heartbeat, power (average) 170 measured by the average watts per workout. Combination cognitive and physical metrics may be provided, such as rate of perceived exertion (RPE) 170 as computed from inputs provided during a self-assessment at the end of the workout and Perception Gap (P-GAP) 168 computed by comparing the athlete's self-assessment inputs from the end of the workout 162, 164 (FIG. 10) with their cognitive 168 and physical metrics 170 (FIG. 11).

Figure 12:
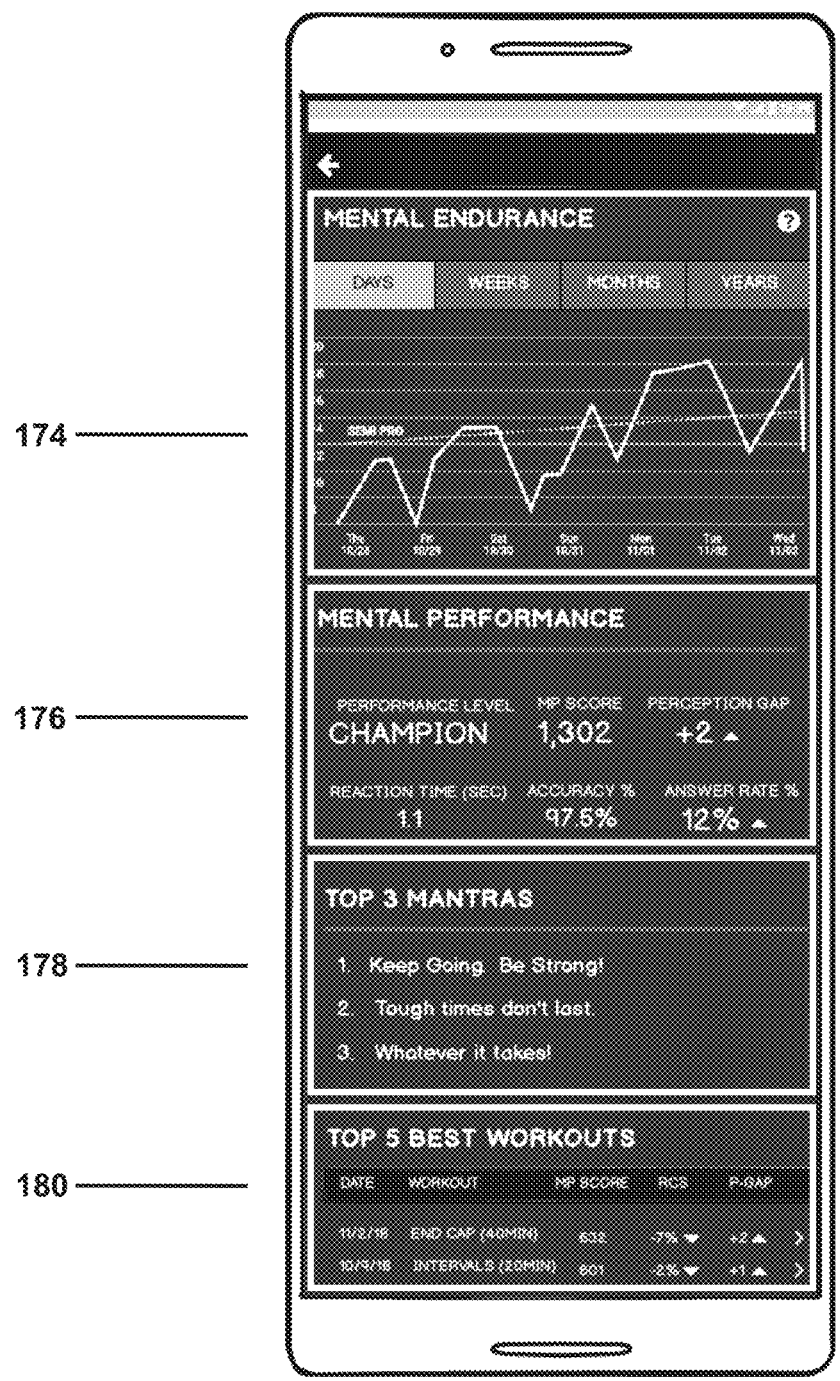
FIG. 12 illustrates an exemplary embodiment of a user interface supporting cognitive and physiological performance reports including workout history and performance over time for all workouts using a computing device such as a smartphone or desktop computer.

FIG. 12 shows the athlete's cumulative report for all workouts over time that includes a chart of their self-rated vs. physical performance over time 174, a summary of their cognitive metrics for all workouts 176, a list of their top 3 mantras 178 and their top 5 best workouts 180 of all time. Both the end of workout report (FIG. 11) and the summary of all workouts over time (FIG. 12) utilize metrics, formulas and algorithms based on a series of lookup tables (FIG. 13). For example, The Perception Gap (P-Gap) metric which is used to chart the athlete's mental endurance in 174 (FIG. 12) and their workout assessment 166 (FIG. 11) uses lookup tables in FIG. 13 to compare their subjective rate of perceived exertion (RPE) that they record at the end of their workout 162 (FIG. 10) with their expected RPE based on physiological output metrics recorded during the workout such as their average power recorded in watts 182 (FIG. 13) or average heart rate recorded in beats per minute 186. For example, if the athlete's subjective RPE is 12 and their average power for the workout is 151 watts then the perception gap algorithm first determines the athlete's expected RPE, by matching their average power from the workout with the closest matching value in the lookup table 184 (FIG. 13). In this case, the athlete's average power most closely matched an average FTP % of 55%, equivalent to an average power of 150 watts which corresponds to an expected RPE value of 9. Lastly, to determine the perception gap value the athlete's self-rated RPE of 12 is subtracted from their expected RPE of 9 generating a perception gap score of −3. In other words, the athlete's subjective rate of perceived exertion (RPE) was inflated by 3 points above what should be expected based on their physiological training output measured in average power indicating that the athlete had a low level of resistance to cognitive fatigue during training.

Another metric used to measure cognitive performance is called Reaction Time (RT) which is the time measured in seconds that it takes the athlete to respond correctly to a given cognitive task question. When a cognitive task question is generated, a date object is created. Every time an athlete answers a question, a time interval measuring the difference between the date/time of when the question was asked and when it was answered is saved in an array. At the end of the interval, the average values from this array are calculated and saved. At the end of the workout, the average response time is calculated for all of the intervals by iterating through intervals, adding the sum of the response times (only if the interval average is greater than 0), and dividing by the total number of these intervals.

Yet another metric used to measure cognitive performance is Accuracy (AC) which is the percentage of correct answers to cognitive questions compared to the total number of questions for a given interval or workout. Every time an athlete answers a question the software determines if the answer was correct or incorrect and saves the total correct and total incorrect for current interval. At the end of the interval, the total number of correct answers are added together and are divided by the total number of answers then multiplied by 100 to create the accuracy percentage score (AC). At the end of the workout, the average accuracy is calculated for all of the intervals by iterating through intervals, adding the sum of the accuracy scores (only if the interval average is greater than 0), and dividing by the total number of these intervals.

III. Motivational Self-Talk

Figure 14:
FIG. 14 illustrates an exemplary embodiment of a user interface supporting positive self-talk mantras that are displayed during training sessions using a portable computing device such as a smartphone.
Figure 15:
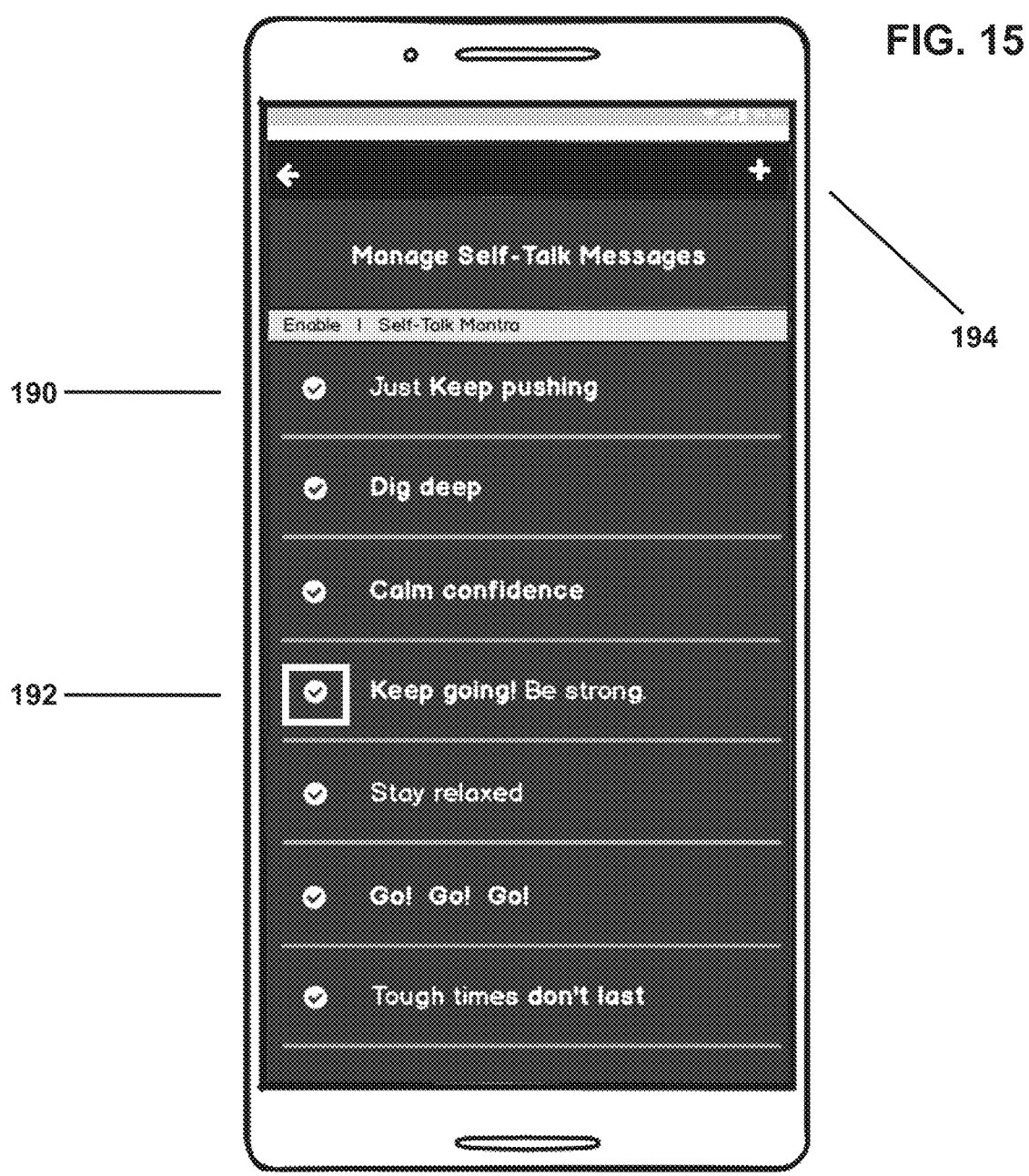
FIG. 15 illustrates an exemplary embodiment of a user interface supporting the configuration and personalization of positive self-talk mantras that are displayed during training sessions using a computing device such as a smartphone or desktop computer.

Another feature supported within the custom software application is the integration of self-talk mantras 188 (FIG. 14) that are designed to provide psychological-based encouragement at specific intervals during the workout. In FIG. 15 the self-talk mantra feature can be configured and personalized by the athlete with specific mantras 190 that are created by the athlete by pressing on the "+" symbol 194 in the top right corner of the screen, entering the mantra with the keyboard of a smartphone or a computer then selecting the mantra with the checkbox 192 that is on the same line directly to the left of the mantra in order to enable it within the feature. The self-talk mantras are also captured and correlated with real-time metrics and cognitive and physiological performance metrics, formulas and algorithms in order to identify the efficacy of each mantra in terms of helping to improve the motivation and performance of the athlete. The top three mantras are then displayed on the cumulative report for all workouts over time 178 (FIG. 12). Additionally, the top performing mantras are adapted within the software to display at a higher frequency during the most difficult stages of the workout to help improve the athlete's cognitive and physical performance. For example, if the athlete is under performing within a complex cognitive task or physically demanding target goal the software will briefly interrupt the workout in order to display a specific mantra that in prior workouts has been correlated with better performance. After the mantra is displayed the software will further score the mantra's efficacy in terms of its impact in improving performance within a short time period after it is displayed.

IV. Cognitive Recovery

Figure 17:
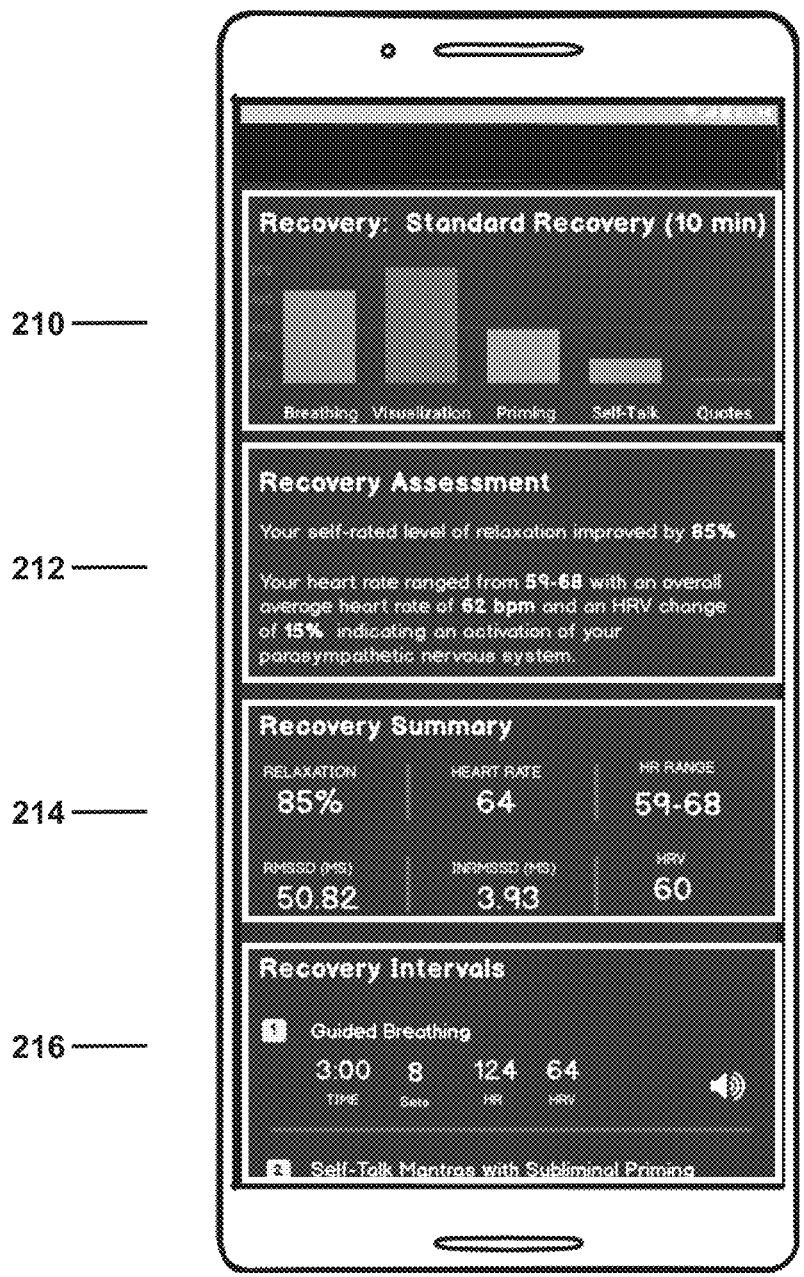
FIG. 17 illustrates an exemplary embodiment of a user interface supporting cognitive and physiological recovery metrics, formulas and algorithms to be recorded and calculated using a computing device such as a smartphone or desktop computer.

At various times during or after brain training the athlete may engage with different combinations of cognitive recovery and motivation protocols (FIGS. 16A and 16B). In the case of using cognitive recovery during training, an athlete may use one or more of the recovery protocols during the rest period between training intervals or as preparation for competition as part of the warm up or warm down process during training. In the case of using cognitive recovery after a brain training session, an athlete may use one or more of the recovery protocols as a form of recuperation after a difficult brain training workout. The recovery protocols can be selected from the recovery category screen 206 (FIG. 16A) and include recovery protocol options such as guided breathing 196, visualization 198, binaural beats 200, subliminal priming 202 and self-talk mantras 204. The recovery and motivation software combines these different recovery protocols into a single interface 208 (FIG. 16B) which is capable of playing each protocol in a sequence one after another based on a predetermined pattern for each recovery session. The recovery and motivation software then uses a series of metrics, formulas and algorithms to combine the athlete's self-rated metrics with the real-time cognitive and physiological output metrics to provide reports (FIG. 17) that summarize the athlete's level of recovery during each session and over time as well as a chart showing the proportions of each recovery protocol featured in the completed recovery session 210. For example, in order to calculate the athlete's subjective self-rated level of relaxation found within the "Recovery Assessment" portion of the report 212, the athlete is asked at both the start and end of each cognitive recovery session to rate their current level of relaxation on a scale of 1-10 where 1 equals "not relaxed" and 10 equals "extremely relaxed". The percent change is then calculated between the athlete's self-rating at the start and end of the session by dividing the absolute value of the difference between the two numbers by the average of those two numbers then multiplying the result by 100 to yield the percent difference e.g. "Your self-rated level of relaxation improved by 85%". For the section of the report labeled "Recovery Summary" 214, various physiological metrics are provided to show the level of physical recovery including heart rate, heart rate range and heart rate variability (HRV). Heart rate is calculated by recording the athlete's heart rate beats per minute (BPM) using an external heart rate monitor or strap that is paired with the recovery software then by calculating the average heart rate by taking the sum of all heart rate values divided by the total number of values. Heart rate range is calculated by an algorithm that scans all of the individual heart rate values and sorts them from the lowest to the highest then takes the first and last values to represent the heart rate range e.g. lowest heart rate value compared to highest heart rate value. Heart rate variability (HRV) is calculated by an algorithm which first measures the time interval between heart beats in milliseconds, then calculates each successive time difference between heartbeats in milliseconds, then squares each of the values, then averages the result, then calculates the square root of the total result, then applies a natural logarithm and lastly applies a scale factor to the logarithm in order to create 0-150 point scale to be displayed in the recovery summary report. An interval summary is also provided within the "Recovery Intervals" section of the report 216, which lists metrics for each interval such as the total number of seconds, total number of sets or cycles of the given protocol, the heart rate (average) for each interval, and the HRV for each interval. All of the metrics provided in the recovery report (FIG. 17) are compared against a baseline average for each individual metric and the positive or negative percent change of each measure factored into the software's evaluation of the effectiveness of the recovery session for the athlete.

V. Cognitive Fatigue Assessment

At various times during or after brain training the athlete may complete a cognitive fatigue self-assessment test (FIGS. 18A and 18B) in order to understand their current level of mental fatigue when compared to their baseline. The software will continuously adapt to the results of the cognitive assessments completed by the athlete, for example if the athlete completes a cognitive fatigue assessment with a result indicating that there has been a decline in their cognitive performance then the software will adapt to recommend an increase in the frequency of cognitive recovery sessions and a decrease in the number of cognitive brain training workouts. As the athlete's cognitive assessment scores improve the software will increase the recommendation to add more cognitive brain training workouts in order to optimize the volume of cognitive stimuli for athletic performance. The cognitive fatigue self-assessment test works by providing output to a user guiding the user through a cognitive testing protocol, such as is illustrated on user interface 218 (FIG. 18A), such as a short reaction time or Go/No Go cognitive task combined with psychological-based questions 220 (FIG. 18B) and physiological measures such as average heart rate and heart rate variability (HRV). For example, as part of a cognitive fatigue assessment, an athlete may complete a short cognitive test such as a simple reaction time test, as illustrated on user interface 218, where the athlete presses one of the tactile-based input apparatus buttons every time they see any stimulus such as a predetermined shape or set of alphanumeric characters. After completing the short cognitive test they will also be asked several psychological questions 220 such as how rested they feel 220, their level of readiness to perform athletic training 220, their current level of stress 220 and current level of frustration 220. In this example, user inputs representing answers to psychological questions will be acquired with software rendering a sliding input scale such as a visual analog scale 220 with simple tick marks indicating levels of gradation from very low to very high. Alternatively or additionally, the fatigue assessment system may measure the athlete's physiological metrics such as their average heart rate, heart rate variability (HRV) and other related physiological measures for the duration of the test. All of these data points may then be used to compare against the athlete's baseline average from previous tests to provide an overall cognitive fatigue score along with a cognitive training and recovery recommendation so that the athlete can assess their current state of readiness to perform a training workout or compete in a competitive event. The recommendations provided as part of the cognitive assessment based on the overall cognitive fatigue score may also be used by the software to adjust the level of difficulty of the cognitive tasks by increasing or decreasing the level of complexity of the task questions, increasing or reducing the amount of time allowed for each question and increasing or decreasing the target score needed to successfully complete a given cognitive task. The software may also adjust the default recommendations for cognitive recovery protocols based on the cognitive fatigue assessment score by increasing or decreasing the default recovery session length and automatically prioritizing certain recovery protocols based on the athlete's needs.

VI. Flowchart of Software Operations

Figure 19:
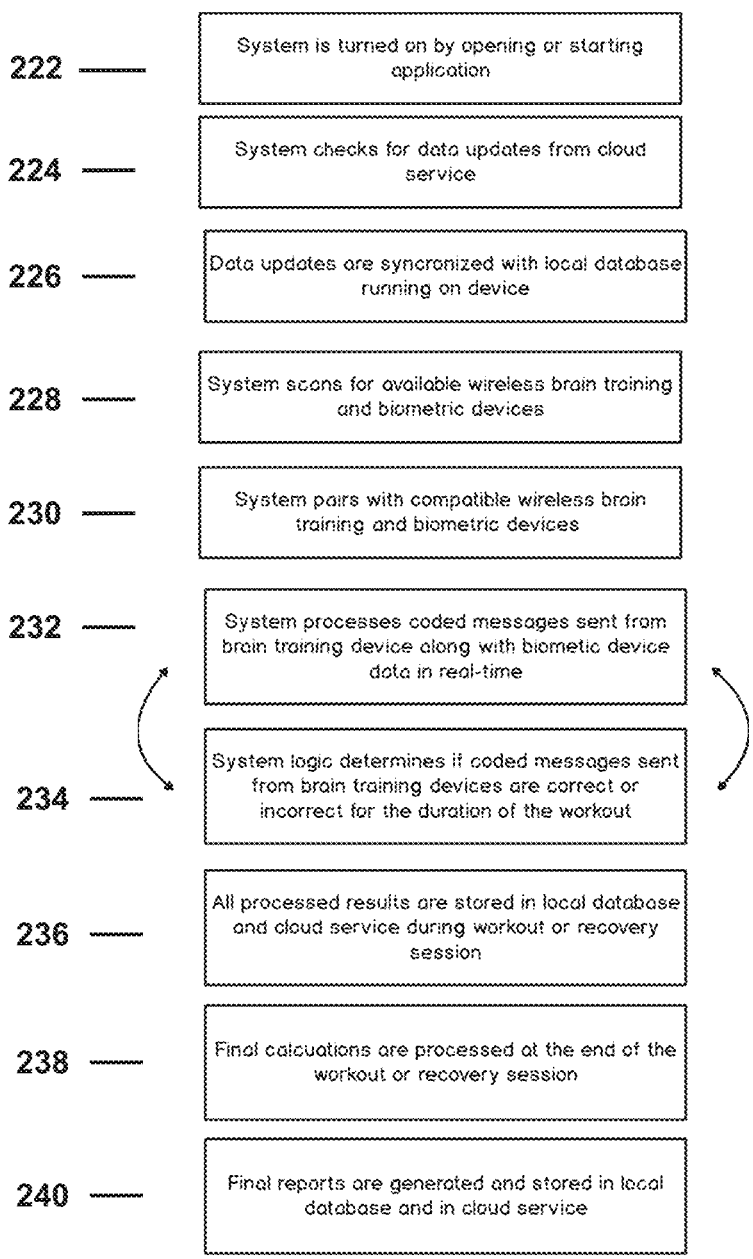
FIG. 19 is a simplified flow diagram of a method of operating software to perform brain training according to some embodiments.

FIG. 19 shows a select sequence of operational steps describing how the software of an athletic training system works. First, the system/application is turned on 222. Next the system checks for data updates from the cloud service 224, next any cloud data updates are synchronized with the local database 226. The system scans for compatible wireless brain training and biometric devices such as a power meter or heart rate monitor 228, and the system pairs with compatible wireless devices 230. The system processes coded messages sent from wireless brain training and biometric devices in real time 232. The system logic determines if coded messages sent from the wireless brain training device(s) represent correct or incorrect answers to the cognitive task questions for the duration of the workout or recovery session 234, next the system processes and stores all results in the local and cloud database 236, next the system performs final calculations at the end of the workout or recovery session 238 and last the system generates final reports that are saved to the local and cloud databases 240.

Additional alternative embodiments of an athletic training system could be created by eliminating all external input devices and relying solely on the built-in sensors and input systems found on a portable computing device such as a smartphone. Such a solution would rely on sensors built into the computing device such as accelerometers, gyroscopes and or capacitive touch screens to provide manual and automated input methods for answering cognitive test questions. For example an athlete may tap on or tilt the screen of a remote computing device in a specific way in order to respond to cognitive test questions during training. In this example, the movement or taps on the screen could be interpreted by the software running on the remote computing device by accessing its sensor data and translating it to the corresponding correct or incorrect answers during cognitive testing. The built-in sensors on the remote computing device may also be used to receive and interpret actions made external to the computing device itself as a method for answering cognitive test questions. For example, the athlete may double tap on the handlebars of their bicycle trainer with their fingers while the portable computing device is mounted to the handlebars. In this example, a double tap on the handlebars by the athlete could be sensed by accelerometer and gyroscope on the portable computing device and interpreted by the custom software that is part of the athletic training system as representing correct or incorrect answers to cognitive test questions during training.

An athletic training system may also be integrated into other training or psychological-based software and hardware to further extend its capabilities or accessibility to athletes for specific sports. For instances where software for guiding a user through cognitive tasks, physical training and/or other actions as described above, is integrated into other software or hardware systems, the input methods for answering cognitive test questions during training may change in order to adapt to the parent software and or hardware being used by the athlete.

The athletic training system described herein could also be adapted as a tool for cognitive therapy for patients suffering from cognitive deficits and disorders such as Parkinson's, ADHD, PTSD, OCD and Autism Spectrum Disorder where inhibitory control and cognitive function have been compromised.

The embodiments above are intended to be illustrative and not limiting. Additional embodiments are within the claims. In addition, although an athletic training system has been described with reference to particular embodiments, those skilled in the art will recognize that changes can be made in form and detail without departing from the spirit and scope of the invention. Thus, the scope of the embodiments should be determined by the appended claims and their legal equivalents, rather than by the examples given.

Example Embodiments

Techniques as described herein may be applied in a method for assessing an athlete's level of cognitive fatigue. The method may comprise: receiving through an interface user responses as a user is guided to perform cognitive tasks; assessing level of cognitive and physical stress based on one or more user inputs in response to prompts presented to the user, the user responses and physiological measurements; assessing the user's cognitive fatigue and outputting a summary of the athlete's cognitive fatigue.

DRAWINGS—REFERENCE NUMERALS 100a bicycle strap for tactile button
100b hand strap for tactile button
102 tactile button
104 button cap
106 waterproof PCB enclosure (top)
108 printed circuit board (PCB)
110 battery
112 waterproof PCB enclosure (bottom)
114 clip for bicycle strap for tactile button
116 bicycle tactile button and strap
118 hand tactile button and strap
120 gesture-based input apparatus
122 motion sensors for gesture-based glove
124 voice commands from user sent to software
126 software interpreting voice commands
128 smartphone computer microphone
130 software interpreting wireless signals
132 smartphone computer receiving Bluetooth wireless signals
134 selection of brain training workouts
136 15 point scale for rating of perceived exertion (RPE)
138 example of level of effort value that the athlete is challenged to produce
140 Example of cognitive task called a Stroop Task
142 left answer button
144 heads up display of target physiological output goals
146 right answer button
148 real-time physiological output metrics
150 software interpreting wireless commands
152 progress bar with target physiological output goals
154 progress bar at rest with 0% value
156 progress bar at 50%
158 progress bar at 100%
160 progress bar at above 100%

162 quantitative rating of perceived exertion (RPE) question
164 qualitative psychological questions
166 workout assessment
168 cognitive metrics
170 physical metrics
172 workout intervals
174 chart of self-rated vs. physical performance
176 summary of cognitive metrics for all workouts
178 top mantras
180 top 5 best workouts
182 functional threshold power (FTP) lookup table
184 example of average athlete power and RPE values
186 lactate threshold heart rate (LTHR) lookup table
188 self-talk mantras interface displayed during workout
190 example of self-talk mantra
192 check box enabling specific self-talk mantra
194 plus symbol for adding new self-talk mantras
196 guided breathing recovery example
198 visualization recovery example
200 binaural beats recovery example
202 subliminal priming recovery example
204 self-talk mantras recovery example
206 recovery category selection screen
208 recovery interface showing how self-talk mantras and subliminal priming protocols
210 recovery chart showing the proportions of each recovery protocol
212 recovery assessment
214 recovery summary
216 recovery intervals
218 cognitive testing protocol for fatigue assessment
220 psychological questions for fatigue assessment
222 system/application is turned on
224 system checks for data updates from cloud service
226 cloud data updates are synchronized with local database
228 system scans for compatible wireless devices
230 system pairs with compatible wireless devices
232 system processes coded messages sent from wireless devices
234 system logic determines correct and incorrect answers
236 system processes and stores all results in database
238 system performs final calculations at the end of the workout or recovery session
240 system generates final reports that are saved to the local and cloud databases.

What is claimed is:

1. A method of operating an athletic training system for improving athletic performance by combining cognitive tasks with physical training and recovery, the athletic training system comprising a computer hardware processor, a user interface coupled to the computer hardware processor, and a device coupled to the computer hardware processor and configured to receive input while a user is performing a physical task, wherein the method comprises:

using the computer hardware processor to perform:
presenting through the user interface a cognitive task for the user to perform, wherein the presenting comprises generating a cognitive task prompt prompting the user to provide an input using the device;
assessing cognitive and physical fatigue of the user based on one or more inputs, wherein assessing cognitive fatigue comprises processing the input received through the device in conjunction with the cognitive task prompt;
identifying one or more cognitive recovery protocols based on the cognitive and physical fatigue of the user; and
presenting through the user interface a prompt guiding the user through a cognitive recovery protocol of the identified one or more cognitive recovery protocols.

2. The method of claim 1, further comprising:
determining an order of the one or more recovery protocols based on the cognitive and physical fatigue of the user; and
presenting through the user interface the one or more recovery protocols in the determined order.

3. The method of claim 1, further comprising adjusting a length of a first recovery protocol of the one or more recovery protocols based on the cognitive and physical fatigue of the user.

4. The method of claim 1, wherein the cognitive task comprises one or more of Stroop Task, Psychomotor Vigilance Task (PVT), Go/No Go Task, Continuous Performance Task (CPT), or Stop Signal Task.

5. A method of operating an athletic training system for improving athletic performance by combining cognitive tasks with physical training, the athletic training system comprising a computer hardware processor, a user interface coupled to the computer hardware processor, and a device coupled to the computer hardware processor and configured to receive input while a user is performing a physical task, wherein the method comprises:

using the computer hardware processor to perform:
presenting through the user interface a cognitive task for the user to perform, wherein the presenting comprises generating a cognitive task prompt prompting the user to provide an input using the device;
assessing cognitive and physical fatigue of the user, wherein assessing the cognitive fatigue of the user comprises processing the input received through the device in relation the cognitive task prompt; and
outputting a recommendation indicative of whether the user is ready to perform a workout based at least in part on assessing the cognitive and physical fatigue of the user.

6. The method of claim 5, wherein assessing the cognitive fatigue of the user comprises:
determining at least one cognitive metric based on the input received through the device in relation to the cognitive task prompt; and
comparing the at least one cognitive metric to at least one stored baseline metric.

7. The method of claim 6, wherein the at least one cognitive metric comprises one or more of reaction time, accuracy, answer rate, or a metric indicative of the reaction time relative to an average reaction time.

8. The method of claim 5, wherein assessing the physical fatigue of the user is performed using a sensor coupled to the computer hardware processor, the assessing comprising:
capturing at least one physiological metric using the sensor; and
comparing the at least one physiological metric to at least one stored baseline metric.

9. The method of claim 8, wherein the at least one physiological metric comprises one or more of heart rate, heart rate variability (HRV), or functional threshold power.

10. The method of claim 5, wherein outputting the recommendation indicative of whether the user is ready to perform the workout comprises:
  processing the input received through the device in relation to the cognitive task prompt and deriving a metric therefrom; and
  comparing the metric to a first threshold indicative of readiness to compete and/or a second threshold indicative of readiness to perform a training workout.

11. The method of claim 5, wherein outputting the recommendation indicative of whether the user is ready to perform the workout comprises presenting, through the user interface, a report indicating whether the user is ready to perform the workout.

12. The method of claim 5, further comprising modifying an aspect of the workout based at least in part on assessing the cognitive and physical fatigue of the user.

13. The method of claim 12, wherein the workout comprises one or more cognitive tasks, and wherein modifying the aspect of the workout comprises increasing or decreasing a number of cognitive tasks included in the workout based on the cognitive and physical fatigue of the user.

14. The method of claim 12, wherein the workout comprises one or more cognitive tasks, and wherein modifying the aspect of the workout comprises adapting difficulty of the one or more cognitive tasks based at least in part on the cognitive and physical fatigue of the user.

15. The method of claim 14, wherein adapting the difficulty of a first cognitive task of the one or more cognitive tasks comprises modifying the first cognitive task to adjust cognitive load for correctly responding to at least one cognitive task prompt of a plurality of cognitive task prompts.

16. The method of claim 14, wherein adapting difficulty of a first cognitive task of the one or more cognitive tasks comprises modifying an amount of time for responding to at least one cognitive task prompt of a plurality of cognitive task prompts.

17. The method of claim 12, wherein the workout comprises one or more cognitive recovery protocols, and wherein modifying the aspect of the workout comprises increasing or decreasing a number of the one or more cognitive recovery protocols included in the workout based at least in part on the cognitive and physical fatigue of the user.

18. The method of claim 17, wherein a recovery protocol of the one or more recovery protocols comprises one or more of guided breathing, visualization, binaural beats, subliminal priming, or self-talk mantras.

19. The method of claim 5, further comprising modifying an aspect of a recovery session based at least in part on assessing the cognitive and physical fatigue of the user, wherein the recovery session comprises one or more cognitive recovery protocols, and wherein modifying the aspect of the recovery session comprises adjusting a length of a first cognitive recovery protocol of the one or more cognitive recovery protocols based on the cognitive and physical fatigue of the user.

20. The method of claim 19, wherein modifying the aspect of the recovery session further comprises performing one or more of: determining a temporal order in which the one or more cognitive recovery protocols should be presented through the user interface based on the cognitive and physical fatigue of the user and determining a duration during which the one or more cognitive recovery protocols should be presented through the user interface based on the cognitive and physical fatigue of the user.

21. The method of claim 5, further comprising:
  presenting, through the user interface, a psychological question for the user to answer; and
  receiving input through the device in relation to the psychological question,
  wherein outputting the recommendation indicative of whether the user is ready to perform a workout based at least in part on assessing the cognitive and physical fatigue of the user comprises outputting the recommendation based on the input received in relation to the psychological question.

22. An athletic training system for improving athletic performance by combining cognitive tasks with physical training, the system comprising:
  a computer hardware processor;
  a device coupled to the computer hardware processor and configured to receive input while a user is performing a physical task;
  a user interface coupled to the computer hardware processor; and
  a non-transitory computer-readable storage medium storing processor executable instructions that, when executed by the processor, cause the computer hardware processor to perform:
    presenting through the user interface a cognitive task for the user to perform, wherein the presenting comprises generating a cognitive task prompt prompting the user to provide an input using the device;
    assessing cognitive and physical fatigue of the user based on one or more inputs, wherein assessing cognitive fatigue comprises processing the input received through the device in conjunction with the cognitive task prompt;
    identifying one or more cognitive recovery protocols based on the cognitive and physical fatigue of the user; and
    presenting through the user interface a prompt guiding the user through a cognitive recovery protocol of the identified one or more cognitive recovery protocols.

* * * * *